(12) United States Patent
Chen et al.

(10) Patent No.: US 10,982,225 B2
(45) Date of Patent: Apr. 20, 2021

(54) FLOWERING TIME-REGULATING GENES AND RELATED CONSTRUCTS AND APPLICATIONS THEREOF

(71) Applicants: PIONEER OVERSEAS CORPORATION, Johnston, IA (US); SINOBIOWAY BIO-AGRICULTURE GROUP CO., LTD., Beijing (CN)

(72) Inventors: Guangwu Chen, Beijing (CN); Yang Gao, Beijing (CN); Shangwu Liang, Beijing (CN); Guihua Lu, Beijing (CN); Guanfan Mao, Beijing (CN); Chao Song, Beijing (CN); Xuguang Tan, Beijing (CN); Changgui Wang, Beijing (CN)

(73) Assignees: PIONEER OVERSEAS CORPORATION; SINOBIOWAY BIO-AGRICULTURE GROUP CO LTD

( * ) Notice: Subject to any disclaimer, the term of this patent is extended or adjusted under 35 U.S.C. 154(b) by 45 days.

(21) Appl. No.: 16/089,449

(22) PCT Filed: Mar. 30, 2017

(86) PCT No.: PCT/CN2017/078795
§ 371 (c)(1),
(2) Date: Sep. 28, 2018

(87) PCT Pub. No.: WO2017/167228
PCT Pub. Date: Oct. 5, 2017

(65) Prior Publication Data
US 2019/0136247 A1    May 9, 2019

(30) Foreign Application Priority Data

Mar. 31, 2016 (CN) .......................... 201610195629.5

(51) Int. Cl.
*C12N 15/82* (2006.01)
*C07K 14/415* (2006.01)
*C12Q 1/68* (2018.01)

(52) U.S. Cl.
CPC .......... *C12N 15/827* (2013.01); *C07K 14/415* (2013.01); *C12N 15/8273* (2013.01); *C12N 15/8274* (2013.01); *C12Q 1/68* (2013.01)

(58) Field of Classification Search
None
See application file for complete search history.

(56) References Cited

U.S. PATENT DOCUMENTS

2015/0252374 A1    9/2015  Danilevskaya et al.
2017/0073699 A1*   3/2017  Poraty-Gavra .... C12N 15/8273

FOREIGN PATENT DOCUMENTS

| CN | 104357453 A | 2/2015 |
| CN | 104447970 A | 3/2015 |
| WO | 2016017194 A1 | 4/2016 |

OTHER PUBLICATIONS

Sauter, Margret, et al. "The novel ethylene-regulated gene OsUsp1 from rice encodes a member of a plant protein family related to prokaryotic universal stress proteins." Journal of Experimental Botany 53.379 (2002): 2325-2331. (Year: 2002).*
Berg et al, Nucleic Acids Research 31 (18): 5291-5304, 2003 (Year: 2003).*
Database Genbank: methyl-CpG-binding domain-containing protein 4 [*Oryza sativa* Japonica Group], Mar. 1, 2016 (Mar. 1, 2016), Database Accession No. XP_015639326.1.
Database Genbank: PREDICTED: *Oryza sativa* Japonica Group methyl-CpG-binding domain-containing protein 4 (LOC4338748), Mar. 1, 2016 (Mar. 1, 2016), Database Accession No. XP_015783840. 1.
Yaish, Mahmoud W., et al.: "The role of epigenetic processes in controlling flowering time in plants exposed to stress", Journal of Experimental Botany, Jun. 1, 2011 (Jun. 1, 2011), vol. 62, No. 11, pp. 3727-3735.
International Search Report for CN Application No. PCT/CN2017/078795, dated Jul. 5, 2017.

* cited by examiner

*Primary Examiner* — Elizabeth F McElwain

(57) ABSTRACT

Isolated polynucleotides and polypeptides, and recombinant DNA constructs useful for regulating plant heading date or flowering time are provided. Compositions (such as plants or seeds) comprising these recombinant DNA constructs, and methods utilizing these recombinant DNA constructs are also provided. The recombinant DNA constructs comprise a polynucleotide operably linked to a promoter that is functional in a plant, wherein said polynucleotides encode flowering time-regulating polypeptides.

5 Claims, 4 Drawing Sheets

Specification includes a Sequence Listing.

FLOWERING TIME-REGULATING GENES AND RELATED CONSTRUCTS AND APPLICATIONS THEREOF

FIELD

This disclosure relates to the field of plant breeding and genetics and, in particular, relates to recombinant DNA constructs useful for regulating flowering time and/or heading date of plants, and methods for the control of flowering time and/or heading date in plants.

BACKGROUND

The growth phase of plants generally includes a vegetative growth phase and a reproductive growth phase. The transition from vegetative to reproductive growth is affected by various flowering signals. The flowering signals are affected by various factors, such as genetic factors such as genotype, and environmental factors such as photoperiod and light intensity, etc. (Dung et al., *Theoretical and Applied Genetics*, 97: 714-720 (1998)).

Flowering time or heading date is an important agronomic trait and is a critical determinant of the distribution and regional adaptability of plants. Most angiosperm species are induced to flower in response to environmental stimuli such as day length and temperature, and internal cues including age.

From the genetic perspective, two phenotypic changes that control vegetative and floral growth are programmed in the plant. The first genetic change involves the switch from the vegetative to the floral state. If this genetic change is not functioning properly, then flowering will not occur. The second genetic event follows the commitment of the plant to form flowers. The observation that the organs of the plant develop on a sequential manner suggests that a genetic mechanism exists in which a series of genes are sequentially turned on and off.

Studies of two distantly related dicotyledons, *Arabidopsis thaliana* and *Antirrhinum majus*, has led to the identification of three classes of homeotic genes, acting alone or in combination to determine floral organ identity (Bowman, et al., *Development*, 112:1 (1991); Carpenter and Coen, *Genes Devl.*, 4:1483 (1990); Schwarz-Sommer, et al., *Science*, 250: 931 (1990)). Several of these genes are transcription factors whose conserved DNA-binding domain has been designated as MADS box (Schwarz-Sommer, et al., supra).

Earlier acting genes that control the identity of flower meristem have also been characterized. Flower meristems are derived from inflorescence meristem in both *Arabidopsis* and *Antirrhinum*. Two factors that control the development of meristematic cells into flowers are known. In *Arabidopsis*, the factors are the products of the LEAFY gene (Weige, et al. Cell 69:843 (1992)) and the APETALA1 gene (Mandel, et al., Nature 360:273 (1992)). When either of these genes is inactivated by mutation, structures combining the properties of flowers and inflorescence develop (Weigel, et al., supra; Irish and Sussex, Plant Cell, 2:741 (1990)). In *Antirrhinum*, the homologue of the *Arabidopsis* LEAFY gene is FLORICAULA (Coen, et al., *Cell*, 63:1311 (1990)) and that of the APETALA1 gene is SQUAMOSA (Huijser, et al., *EMBO J.*, 11:1239 (1992)). The latter pair contains MADS box domains.

Accelerating or delaying the onset of flowering can be useful to farmers and seed producers. An understanding of the genetic mechanisms which influence flowering provides methods for altering the flowering characteristics of the target plant. Cereals, rice and maize, are agronomically important in warmer climatic zones, and wheat, barley, oats and rye in more temperature climates, with respect to flowering. Important seed products are oil seed rape, canola, sugar beet, maize, sunflower, soybean and sorghum.

SUMMARY

In one aspect, the present disclosure includes an isolated polynucleotide regulating plant flowering time, comprising: (a) a polynucleotide with nucleotide sequence of at least 85% sequence identity to SEQ ID NO: 2 or 5; (b) a polynucleotide with nucleotide sequence of at least 85% sequence identity to SEQ ID NO: 3 or 6; (c) a polynucleotide encoding a polypeptide with amino acid sequence of at least 90% sequence identity to SEQ ID NO: 4 or 7; or (d) the full complement of the nucleotide sequence of (a), (b) or (c), wherein increasing expression of the polynucleotide in plants promotes the transition from vegetative growth to reproductive growth; reducing the expression of the polynucleotide in plants prolongs the time of transition from vegetative growth to reproductive growth. The said polynucleotide comprises the nucleotide sequence of SEQ ID NO: 2, SEQ ID NO: 3, SEQ ID NO: 5 or SEQ ID NO: 6. The said polynucleotide encodes polypeptides comprising the amino acid sequence of SEQ ID NO: 4 or SEQ ID NO: 7. Further, increased expression of this polynucleotide increases paraquat tolerance and grain yield of the plants after drought stress.

In another aspect, the present disclosure includes a recombinant DNA construct comprising the isolated polynucleotide operably linked to at least one heterologous regulatory sequence, wherein the polynucleotide comprises (a) a polynucleotide with nucleotide sequence of at least 85% sequence identity to SEQ ID NO: 2, 3, 5 or 6; (b) a polynucleotide encoding a polypeptide with amino acid sequence of at least 90% sequence identity to SEQ ID NO: 4 or 7; or (c) the full complement of the nucleotide sequence of (a) or (b); the at least one heterologous regulatory sequence is a promoter functional in a plant.

In another aspect, the present disclosure includes a plant or seed comprising a recombinant DNA construct comprising the polynucleotide operably linked to at least one heterologous regulatory sequence, wherein the polynucleotide comprises (a) a polynucleotide with nucleotide sequence of at least 85% sequence identity to SEQ ID NO: 2, 3, 5 or 6; (b) a polynucleotide encoding a polypeptide with amino acid sequence of at least 90% sequence identity to SEQ ID NO: 4 or 7; or (c) the full complement of the nucleotide sequence of (a) or (b).

In another aspect, the present disclosure includes a modified plant or plant cell with altered expression of at least one polynucleotide encoding a MBD1 or USP1 polypeptide, wherein the plant exhibits altered flowering trait when compared to a control plant planted under the same conditions. Increasing expression of the polynucleotide in plants promotes the transition from vegetative growth to reproductive growth; reducing the expression of the polynucleotide in plants prolongs the time of transition from vegetative growth to reproductive growth.

The plant comprising in its genome a recombinant DNA construct comprising a polynucleotide operably linked to at least one heterologous regulatory element, wherein the polynucleotide comprises (a) a polynucleotide with nucleotide sequence of at least 85% sequence identity to SEQ ID NO: 2, 3, 5 or 6; (b) a polynucleotide encoding a polypeptide with amino acid sequence of at least 90% sequence identity to SEQ ID NO: 4 or 7; or (c) the full complement of the nucleotide sequence of (a) or (b), wherein the said plant exhibits altered flowering time when compared to a control plant, over-expression of the polynucleotide in the said plants promotes the transition from vegetative growth to reproductive growth; reducing the expression of the polynucleotide in the said plants prolongs the time of transition from vegetative growth to reproductive growth.

The plant can be obtained by editing the promoter sequence to increase expression of polypeptide with amino acid sequence of identity of at least 90% to SEQ ID NO: 4 and 7, increasing expression of the polynucleotide in plant promotes earlier flowering time when compared to a control plant.

In another aspect, the present disclosure includes any of the plants of the disclosure, wherein the plant is selected from the group consisting of rice, maize, soybean, sunflower, sorghum, canola, wheat, alfalfa, cotton, barley, millet, sugar cane and switchgrass.

In another aspect, methods are provided for regulating plant flowering time, comprising altering the expression of at least one polynucleotide encoding a MBD1 or USP1 polypeptide in the rice plant, wherein the polynucleotide comprises: (a) a polynucleotide with nucleotide sequence of at least 85% sequence identity to SEQ ID NO: 2 or 5; (b) a polynucleotide with nucleotide sequence of at least 85% sequence identity to SEQ ID NO: 3 or 6; and (c) a polynucleotide encoding a polypeptide with amino acid sequence of at least 90% sequence identity to SEQ ID NO: 4 or 7, increasing expression of the polynucleotide in the said plants promotes the transition from vegetative growth to reproductive growth; reducing the expression of the polynucleotide in the said plants prolongs the time of transition from vegetative growth to reproductive growth.

The expression of the polynucleotide is altered by a step selected from the group consisting of: (a) increasing the expression of the polynucleotide encoding a MBD1 or USP1 polypeptide in plant by a recombinant DNA construct, wherein the recombinant DNA construct comprises the polynucleotide encoding the MBD1 or USP1 polypeptide operably linked to at least one heterologous regulatory sequence, wherein the polynucleotide encodes the polypeptide having an amino acid sequence of at least 90% sequence identity compared to SEQ ID NO: 4 or 7; (b) increasing or decreasing the expression of an endogenous polynucleotide encoding the polypeptide having an amino acid sequence of at least 90% sequence identity compared to SEQ ID NO: 4 or 7; and (c) decreasing the expression of the polynucleotide encoding a MBD1 or USP1 polypeptide in plant by a recombinant DNA construct, wherein the recombinant DNA construct comprises a silencing element that down regulates the expression of an endogenous polynucleotide encoding the polypeptide having an amino acid sequence of at least 90% sequence identity compared to SEQ ID NO: 4 or 7.

In another aspect, methods are provided for increasing drought tolerance in a plant, comprising increasing the expression of at least one polynucleotide encoding a MBD1 or USP1 polypeptide in the plant. the expression of the polynucleotide is increased by a step selected from the group consisting of: (a) increasing the expression of the polynucleotide encoding a MBD1 or USP1 polypeptide in plant by a recombinant DNA construct, wherein the recombinant DNA construct comprises the polynucleotide encoding the MBD1 or USP1 polypeptide operably linked to at least one heterologous regulatory sequence, wherein the polynucleotide encodes the polypeptide having an amino acid sequence of at least 90% sequence identity compared to SEQ ID NO: 4 or 7; and (b) increasing the expression of an endogenous polynucleotide encoding the polypeptide having an amino acid sequence of at least 90% sequence identity compared to SEQ ID NO: 4 or 7. Improved drought tolerance may be due to increased survival rate, reduced leaf rolling degree, improved seed setting rate, or increased grain yield under drought condition.

In another aspect, the present disclosure concerns a recombinant DNA construct comprising any of the isolated polynucleotides of the present disclosure operably linked to at least one regulatory sequence, and a cell, a plant, and a seed comprising the recombinant DNA construct. The cell may be eukaryotic, e.g., a yeast, insect or plant cell, or prokaryotic, e.g., a bacterium.

BRIEF DESCRIPTION OF THE DRAWINGS AND SEQUENCE LISTINGS

The disclosure can be more fully understood from the following detailed description and the accompanying drawings and Sequence Listing which form a part of this application.

FIG. 1 shows the relative expression levels of OsMBD1 gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured Zhonghua 11, ZH11-WT is wild type Zhonghua11, and DP0158 is transformed with empty vector DP0158.

FIG. 2 shows the relative expression levels of OsUSP1 gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured Zhonghua 11, ZH11-WT is wild type Zhonghua11, and DP0158 is transformed with empty vector DP0158.

Figure 1:
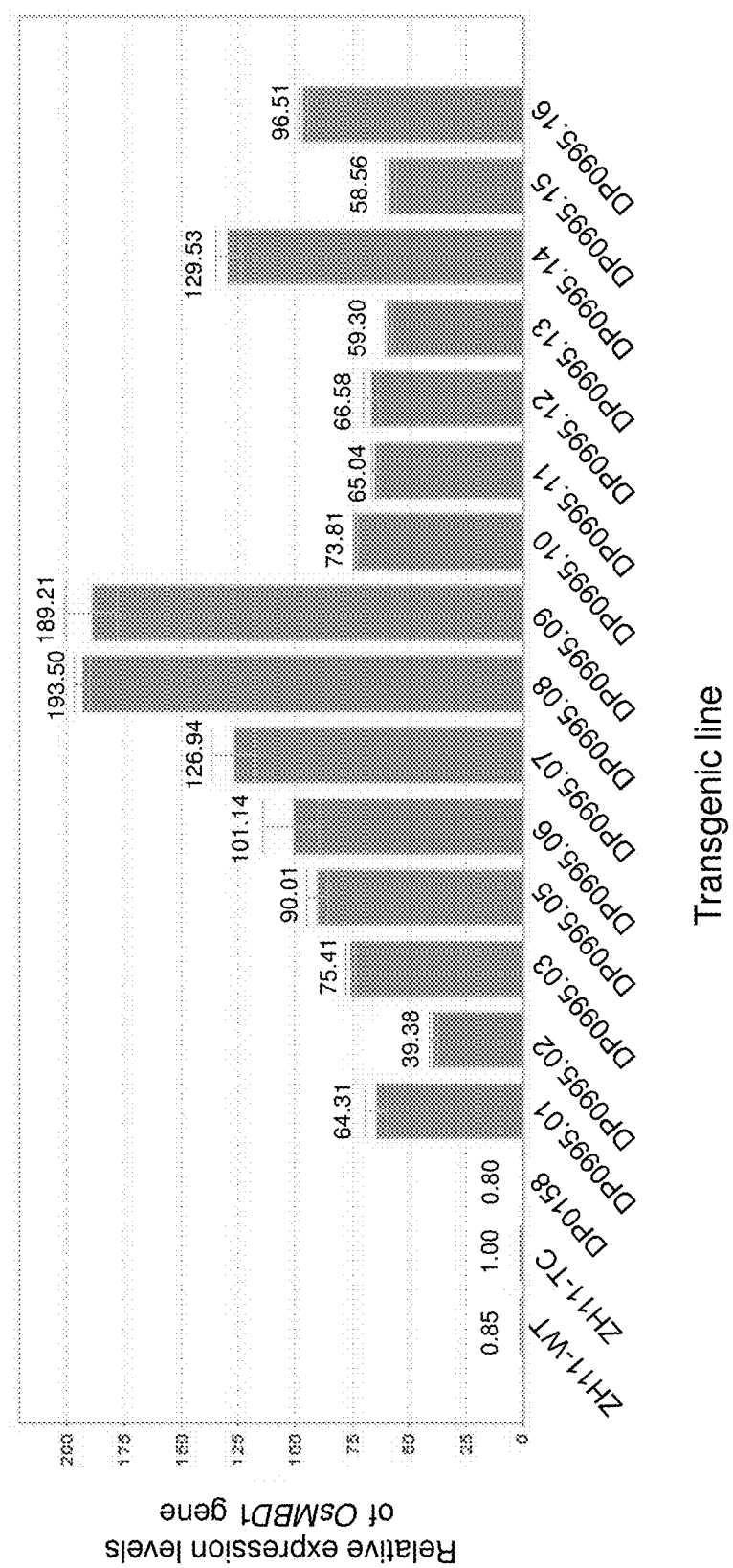

Table 1. SEQ ID NOs for nucleotide and amino acid sequences provided in the sequence Table 2. Primers for cloning rice flowering time-regulating genes Table 3. PCR reaction mixture Table 4. PCR cycle conditions for cloning rice flowering time-regulating genes Table 5. Flowering trait, plant height and grain yield of OsMBD1 transgenic rice plants at $T_1$ generation in Beijing Table 6. Grain yield analysis of OsMBD1 transgenic rice plants at $T_1$ generation and at construct level Table 7. Plant height analysis of OsMBD1 transgenic rice plants at $T_1$ generation and at construct level Table 8. Effective panicle number analysis of OsMBD1 transgenic rice plants at $T_1$ generation and at construct level Table 9. Flowering trait and grain yield analysis of OsMBD1 transgenic rice at T1 generation in Hainan Table 10. Flowering trait, plant height and grain yield analysis of OsMBD1 transgenic rice plant at $T_1$ generation in Beijing ($2^{nd}$ experiment)

Table 11. Flowering trait, plant height and grain yield analysis of OsMBD1 transgenic rice plants at $T_1$ generation in Ningxia Table 12. Flowering trait and grain yield analysis of OsMBD1 transgenic rice at $T_2$ generation in Hainan Table 13. Flowering trait, plant height and grain yield analysis of OsMBD1 transgenic rice plants at $T_2$ generation in Beijing ($1^{st}$ experiment)

Table 14. Flowering trait, plant height and grain yield analysis of OsMBD1 transgenic rice plants at $T_2$ generation in Beijing ($2^{nd}$ experiment)

Table 15. Flowering trait, plant height and grain yield analysis of OsMBD1 transgenic rice at $T_2$ generation in Ningxia Table 16. Grain yield analysis of OsMBD1 transgenic rice plants under field drought conditions ($1^{st}$ experiment)

Table 17. Grain yield analysis of OsMBD1 transgenic rice plants under field drought conditions ($2^{nd}$ experiment)

Table 18. Flowering trait, plant height and grain yield analysis of OsUSP1 transgenic rice plants at $T_1$ generation in Beijing Table 19. Grain yield analysis of OsUSP1 transgenic rice plants at $T_1$ generation at construct level Table 20. Plant height analysis of OsUSP1 transgenic rice plants at $T_1$ generation at construct level Table 21. Effective panicle number analysis of OsUSP1 transgenic rice plants at $T_1$ generation at construct level Table 22. Flowering trait and grain yield analysis of OsUSP1 transgenic rice plants at $T_1$ generation in Hainan Table 23. Flowering trait, plant height and grain yield analysis of OsUSP1 transgenic rice plant at $T_1$ generation in Beijing ($2^{nd}$ experiment)

Table 24. Flowering trait, plant height and grain yield analysis of OsUSP1 transgenic rice plants at $T_1$ generation in Ningxia Table 25. Flowering trait, plant height and grain yield analysis of OsUSP1 transgenic rice plant at $T_2$ generation in Hainan Table 26. Flowering trait, plant height and grain yield analysis of OsUSP1 transgenic rice plant at $T_2$ generation in Beijing ($1^{st}$ experiment)

Table 27. Flowering trait, plant height and grain yield analysis of OsUSP1 transgenic rice plant at $T_2$ generation in Beijing ($2^{nd}$ experiment)

Table 28. Flowering trait, plant height and grain yield analysis of OsUSP1 transgenic rice plants at $T_2$ generation in Ningxia Table 29. Grain yield analysis of OsUSP1 transgenic rice plants under field drought conditions Table 30. Paraquat tolerance assay of OsMBD1 transgenic rice plants ($1^{st}$ experiment)

Table 31. Paraquat tolerance assay of OsMBD1 transgenic rice plants ($2^{nd}$ experiment)

Table 32. Paraquat tolerance assay of OsUSP1 transgenic rice plants ($1^{st}$ experiment)

Table 33. Paraquat tolerance assay of OsUSP1 transgenic rice plants ($2^{nd}$ experiment)

TABLE 1

SEQ ID NOs for nucleotide and amino acid sequences provided in the sequence listing

| Source species | Clone Designation | SEQ ID NO: (Nucleotide) | SEQ ID NO: (Amino Acid) |
|---|---|---|---|
| Artificial sequence | DP0158 vector | 1 | n/a |
| Oryza sativa | OsMBD1 | 2, 3 | 4 |
| Oryza sativa | OsUSP1 | 5, 6 | 7 |
| Artificial | Primers | 8-15 | n/a |

The sequence descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

SEQ ID NO: 1 is the nucleotide sequence of vector DP0158.
SEQ ID NO: 2 is the nucleotide sequence of cDNA of OsMBD1 gene.
SEQ ID NO: 3 is the nucleotide sequence of CDS of OsMBD1 gene.
SEQ ID NO: 4 is the amino acid sequence of OsMBD1.
SEQ ID NO: 5 is the nucleotide sequence of cDNA of OsUSP1 gene.
SEQ ID NO: 6 is the nucleotide sequence of CDS of OsUSP1 gene.
SEQ ID NO: 7 is the amino acid sequence of OsUSP1.
SEQ ID NO: 8 is forward primer for cloning cDNA of OsMBD1 gene.
SEQ ID NO: 9 is reverse primer for cloning cDNA of OsMBD1 gene.
SEQ ID NO: 10 is forward primer for cloning cDNA of OsUSP1 gene.
SEQ ID NO: 11 is reverse primer for cloning cDNA of OsUSP1 gene.
SEQ ID NO: 12 is forward primer for real-time RT-PCR analysis of OsMBD1 gene.
SEQ ID NO: 13 is reverse primer for real-time RT-PCR analysis of OsMBD1 gene.
SEQ ID NO: 14 is forward primer for real-time RT-PCR analysis of OsUSP1 gene.
SEQ ID NO: 15 is reverse primer for real-time RT-PCR analysis of OsUSP1 gene

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

As used herein:

The term "OsMBD1" is a methyl-binding domain protein 1 (MBD1) and refers to a rice polypeptide that regulates rice flowering trait and is encoded by the rice gene locus LOC_Os05g33550.1. "MBD1 polypeptide" refers herein to the OsMBD1 polypeptide and its homologs from other organisms.

The OsMBD1 polypeptide (SEQ ID NO: 4) is encoded by the coding sequence (CDS) (SEQ ID NO: 3) or nucleotide sequence (SEQ ID NO: 2) at rice gene locus LOC_Os05g33550.1. This polypeptide is annotated as "methyl-binding domain protein MBD, putative, expressed" in TIGR (the internet at plant biology msu.edu/index.shtml), however does not have any prior assigned function.

The term "OsUSP1 (universal stress protein 1)" refers to a rice polypeptide that regulates rice flowering characteristics and is encoded by the rice gene locus LOC_Os07g36600.1. "USP1 polypeptide" refers herein to the OsUSP1 polypeptide and its homologs from other organisms.

The OsUSP1 polypeptide (SEQ ID NO: 7) is encoded by the coding sequence (CDS)

(SEQ ID NO: 6) or nucleotide sequence (SEQ ID NO: 5) at rice gene locus LOC_Os07g36600.1. This polypeptide is annotated as "universal stress protein domain containing protein, putative, expressed" in TIGR, however does not have any prior assigned function.

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

"Flowering" refers to the process of anthesis, i.e. glume dehiscent and anthers scattering under suitable temperature and humidity, or the process of flower formation. Herein flowering is used to referring the process from young panicle differentiation, maturation, to the panicle heading.

"Flower development" or "floral development" is intended to mean the development of a flower or inflorescence from the initiation of the floral meristem to the development of the mature flower.

"Reproductive development" is intended to mean the development of a flower or inflorescence from the initiation of the floral meristem through pollination and the development of mature fruit.

Plants having an "early flowering time" as used herein are plants which start to flower earlier than control plants. Hence this term refers to plants that show an earlier start of flowering. Flowering time of plants can be assessed by counting the number of days (time to flower) between sowing and the emergence of a first inflorescence. The "flowering time" of a plant can for instance be readily determined using known methods and standards.

"Heading" used herein refers the process of cereal panicle extended from flag leaf sheath.

"Heading date" and "heading time" are used interchangeably herein, and refers to the number of days from the day of seeding to the day when 50% young panicle of an individual plant head out the flag leaf sheath. Heading date is an important agronomic trait, which is under the regulation of basic nutritional genes and photoperiod-sensitivity genes and plays a key role in the adaptation and geo-graphic distribution of rice varieties. Appropriate heading date is a prerequisite for attaining the desired yield level.

The rice panicle will flower after the panicle headed out under normal condition. Herein heading date will be used to indicate the flowering time.

"Plant height" as used herein refers to the height from the surface of the field to the top of the highest panicle or leaf of an individual plant.

The terms "full complement" and "full-length complement" are used interchangeably herein, and refer to a complement of a given nucleotide sequence, wherein the complement and the nucleotide sequence consist of the same number of nucleotides and are 100% complementary.

The term "trait" refers to a physiological, morphological, biochemical, or physical characteristic of a plant or particular plant material or cell.

"Agronomic characteristic" is a measurable parameter including but not limited to: greenness, grain yield, growth rate, total biomass or rate of accumulation, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress.

"Transgenic" refers to any cell, cell line, callus, tissue, plant part or plant, the genome of which has been altered by the presence of a recombinant DNA construct.

A "control" or "control plant" or "control plant cell" provides a reference point for measuring changes in phenotype of a subject plant or plant cell which was genetically altered by, such as transformation, and has been affected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed.

In this disclosure, ZH11-WT, ZH11-TC and empty vector plants may be designated as control plants. ZH11-WT represents wild type Zhonghua 11, ZH11-TC represents rice plants generated from tissue cultured Zhonghua 11, and empty vector represents plants transformed with empty vector DP0158.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Heterologous" with respect to sequence means a sequence that originates from a foreign species, or, if from the same species, is substantially modified from its native form in composition and/or genomic position by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases.

The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Mature" protein refers to a post-translationally processed polypeptide; i.e., one from which any pre- or pro-peptides present in the primary translation product has been removed.

"Precursor" protein refers to the primary product of translation of mRNA; i.e., with pre- and/or pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a cDNA. In some embodiments, the non-genomic nucleic acid molecule is a synthetic nucleic acid sequence.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" and "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably and refer to a promoter that is expressed predominantly but not necessarily exclusively in one tissue or organ, but that may also be expressed in one specific cell.

"Developmentally regulated promoter" refers to a promoter whose activity is determined by developmental events.

"Genetic modification" refers to a change or alteration in the genomic nucleic acid sequence of a plant introduced by deliberate human activity.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) Ann. Rev. Plant Phys. Plant Mol. Biol. 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627-1632). A "mitochondrial signal peptide" is an amino acid sequence which directs a precursor protein into the mitochondria (Zhang and Glaser (2002) Trends Plant Sci 7:14-21).

DNA nucleases and other mutation enzyme domains may be fused with DNA binding domains to produce the double strand break (DSBs) in the target DNA. DNA binding domains include, for example, an array specific DNA binding domain or a site-specific DNA binding domain. Site specific DNA binding domain include but are not limited to a TAL (Transcription Activator-Like Effector) or a zinc finger binding domain.

Examples of DNA-binding domains fused to DNA nucleases include but are not limited to TALEN and multiple TALENs. Transcription Activator-Like Effector Nucleases (TALENs) are artificial restriction enzymes generated by fusing the TAL effector DNA binding domain to a DNA enzyme domain. TAL proteins are produced by bacteria and include a highly conserved 33-34 amino acid DNA binding domain sequence (PCT publication No. WO2014127287; US Patent Publication No. US20140087426).

The original TALEN chimera were prepared using the wild-type FokI endonuclease domain. However, TALEN may also include chimera made from Fok1 endonuclease domain variants with mutations designed to improve cleavage specificity and cleavage activity. In some instances multiple TALENs can be expressed to target multiple genomic regions.

A zinc finger is another type of DNA binding domain that can be used for introducing mutations into the target DNA.

Various protein engineering techniques can be used to alter the DNA-binding specificity of zinc fingers and tandem repeats of such engineered zinc fingers can be used to target desired genomic DNA sequences. Fusing a second protein domain such as a transcriptional repressor to a zinc finger that can bind near the promoter of the YEP gene can reduce the expression levels of MBD1 and USP1 gene.

In one embodiment, a regulatory element driving the endogenous gene expression or the coding sequence itself, for example, may be edited or inserted into a plant by genome editing using a CRISPR/Cas9 system.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

Cas gene relates to a gene that is generally coupled, associated or close to or in the vicinity of flanking CRISPR loci. The terms "Cas gene", "CRISPR-associated (Cas) gene" are used interchangeably herein. (Haft et al. (2005) Computational Biology, PLoS Comput Biol 1(6): e60. doi: 10.1371/journal.pcbi.0010060). As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by a guide polynucleotide to recognize and optionally introduce a double strand break at a specific target site into the genome of a cell (U.S. 2015/0082478). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence. The Cas endonuclease can be introduced directly into a cell by any method known in the art, for example, but not limited to transient introduction methods, transfection and/or topical application.

As used herein, the term "guide RNA" relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site (U.S. 2015/0082478). The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited to, Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

Turning now to the embodiments:

Embodiments include isolated polynucleotides and polypeptides, recombinant DNA constructs useful for regulating plant flowering time, compositions (such as plants or seeds) comprising these recombinant DNA constructs, and methods utilizing these recombinant DNA constructs.

Isolated Polynucleotides and Polypeptides

The present disclosure includes the following isolated polynucleotides and polypeptides:

In some embodiments, polynucleotides are provided encoding MBD1 polypeptides or USP1 polypeptides.

In some embodiments, isolated polynucleotides are provided comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 4 or 7; or (ii) a full complement of the nucleic acid sequence of (i), wherein the full complement and the nucleic acid sequence of (i) consist of the same number of nucleotides and are 100% complementary. Increasing expression of this polynucleotide promotes the transition from vegetative growth to reproductive growth; reducing expression of the polynucleotide prolongs time of transition from vegetative growth to reproductive growth; increasing expression of this polynucleotide increases paraquat tolerance and grain yield of the plants after drought stress. Any of the foregoing isolated polynucleotides may be utilized in any recombinant DNA constructs of the present disclosure.

In some embodiments, isolated polypeptides are provided having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 4 or 7. The polypeptides are flowering time-regulating polypeptide MBD1 or USP1.

In some embodiments, isolated polynucleotide are provided comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 2, 3, 5 or 6; or (ii) a full complement of the nucleic acid sequence of (i). Any of the foregoing isolated polynucleotides may be utilized in any recombinant DNA constructs of the present disclosure. The isolated polynucleotide preferably encodes a flowering time-regulating protein. Increasing expression of this polynucleotide promotes the transition from vegetative growth to reproductive growth; reducing expression of the polynucleotide prolongs time of transition from vegetative growth to reproductive growth; increasing expression of this polynucleotide increases paraquat tolerance and grain yield of the transgenic plants after drought stress.

Recombinant DNA Constructs and Suppression DNA Constructs

In one aspect, the present disclosure includes recombinant DNA constructs and suppression DNA constructs.

In one embodiment, a recombinant DNA construct comprises a polynucleotide operably linked to at least one heterologous regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 4 or 7; or (ii) a full complement of the nucleic acid sequence of (i).

In another embodiment, a recombinant DNA construct comprises a polynucleotide operably linked to at least one heterologous regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74.%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity as compared to SEQ ID NO: 2, 3, 5 or 6; or (ii) a full complement of the nucleic acid sequence of (i).

In another embodiment, a recombinant DNA construct comprises a polynucleotide operably linked to at least one heterologous regulatory sequence (e.g., a promoter functional in a plant), wherein said polynucleotide encodes a MBD1 or USP1 protein. This polypeptide regulates flowering time, and may be from, for example, *Oryza sativa*, *Oryza australiensis*, *Oryza barthii*, *Oryza glaberrima* (African rice), *Oryza latifolia*, *Oryza longistaminata*, *Oryza meridionalis*, *Oryza officinalis*, *Oryza punctata*, *Oryza rufipogon* (brownbeard or red rice), *Oryza nivara* (Indian wild rice), *Arabidopsis thaliana*, *Zea mays*, *Glycine max*, *Glycine tabacina*, *Glycine soja* or *Glycine tomentella*.

In another aspect, the present disclosure includes suppression DNA constructs.

A suppression DNA construct may comprise at least one heterologous regulatory element (e.g., a promoter functional in a plant) operably linked to suppression elements, wherein the suppression elements comprise at least 100 contiguous base pairs of (a) (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4 or 7, or (ii) a full complement of the nucleic acid sequence of (a)(i); or (b) a region derived from a sense strand or antisense strand of a target gene of interest, wherein said target gene of interest encodes a flowering time-regulating polypeptide MBD1 or USP1; or (c) (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 2 or 5, or (ii) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 3 or 6, or (iii) a full complement of the nucleic acid sequence of (c)(i) or (c)(ii).

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing", as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, includes lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product.

"Cosuppression" refers to the production of sense RNA transcripts capable of suppressing the expression of the target gene or gene product. "Sense" RNA refers to RNA transcript that includes the mRNA and can be translated into protein within a cell or in vitro.

Another variation describes the use of plant viral sequences to direct the suppression of proximal mRNA encoding sequences (PCT Publication No. WO 98/36083 published on Aug. 20, 1998).

RNA interference (RNAi) refers to the process of sequence-specific post-transcriptional gene silencing in animals mediated by short interfering RNAs (siRNAs) (Fire et al., Nature 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., Trends Genet. 15:358 (1999)).

It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants.

MicroRNAs (miRNAs) are designed that regulate target genes (e.g., the polynucleotide sequences disclosed herein) by binding to complementary sequences located in the transcripts produced by these genes for example by translational inhibition and RNA cleavage.

Regulatory Elements:

A recombinant DNA construct (including a suppression DNA construct) of the present disclosure may comprise at least one regulatory element.

A regulatory element may be a promoter, enhancer, 5'UTR, or 3'UTR.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may (or may not) have pleiotropic effects, although candidate gene efficacy may be estimated when driven by a constitutive promoter. Use of tissue-specific and/or stress-specific promoters may eliminate undesirable effects, but retain the ability to regulate plant flowering time. This type of effect has been observed in Arabidopsis for drought and cold tolerance (Kasuga et al., Nature Biotechnol. 17:287-91 (1999)).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present disclosure which causes the desired temporal and spatial expression.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development, the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Cim1 that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp (WO 00/12733), herein incorporated by reference. Additional early kernel/embryo promoters that find use in certain methods of the present disclosure include the seed-preferred promoter ltp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize lec1 promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007). Additional promoters for regulating the expression of the nucleotide sequences of the present disclosure in plants are stalk-specific promoters. Such stalk-specific promoters include the alfalfa S2A promoter (GenBank Accession No. EF030816; Abrahams et al., *Plant Mol. Biol.* 27:513-528 (1995)) and S2B promoter (GenBank Accession No. EF030817) and the like, herein incorporated by reference.

Promoters for use in the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (GenBank Accession No. EF030817), and the constitutive promoter GOS2 from *Zea mays*. Other promoters include root preferred promoters, such as the maize NAS2 promoter, the maize Cyclo promoter (US Publication No. 2006/0156439, published Jul. 13, 2006), the maize ROOTMET2 promoter (WO 2005/063998, published Jul. 14, 2005), the CR1BIO promoter (WO 2006/055487, published May 26, 2006), the CRWAQ81 promoter (WO 2005/035770, published Apr. 21, 2005) and the maize ZRP2.47 promoter (NCBI Accession No. U38790; NCBI GI No. 1063664).

Recombinant DNA constructs of the present disclosure may also include other regulatory elements including, but not limited to, translation leader sequences, introns, and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)).

An enhancer or enhancer element refers to a cis-acting transcriptional regulatory element, a.k.a. cis-element, which confers an aspect of the overall expression pattern, but is usually insufficient alone to drive transcription, of an operably linked polynucleotide sequence. An isolated enhancer element may be fused to a promoter to produce a chimeric promoter cis-element, which confers an aspect of the overall modulation of gene expression. Enhancers are known in the art and include the SV40 enhancer region, the CaMV 35S enhancer element, and the like. Some enhancers are also known to alter normal regulatory element expression patterns, for example, by causing a regulatory element to be expressed constitutively when without the enhancer, the same regulatory element is expressed only in one specific tissue or a few specific tissues. Duplicating the upstream region of the CaMV35S promoter has been shown to increase expression by approximately tenfold (Kay, R. et al., (1987) Science 236: 1299-1302).

In hybrid seed propagated crops, mature transgenic plants or genome edited plants can be self-pollinated to produce a homozygous inbred plant. The inbred plant produces seed containing the newly introduced recombinant DNA construct. These seeds can be grown to produce plants that would exhibit an altered agronomic characteristic, or used in a breeding program to produce hybrid seed, which can be grown to produce plants that would exhibit such an altered agronomic characteristic. The seeds may be maize seeds, or rice seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley or millet.

The recombinant DNA construct is stably integrated into the genome of the plant.

Embodiments include but are not limited to the following:

1. A transgenic or a genome edited plant (for example, a rice, maize or soybean plant) comprising in its genome a polynucleotide operably linked to at least one heterologous regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 4 or 7; and wherein said plant exhibits altered flowering time when compared to a control plant not comprising a genetic modification or the heterologous regulatory element, increasing expression of the said polynucleotide promotes the transition from vegetative growth to reproduction growth, and reducing expression of the polynucleotide prolongs time of transition from vegetative growth to reproductive growth; increased expression of this polynucleotide increases paraquat tolerance and grain yield of the plants after drought stress.

2. A transgenic plant (for example, a rice, maize or soybean plant) comprising in its genome a suppression DNA construct comprising at least one heterologous regulatory element operably linked to suppression elements, wherein the suppression elements derives from a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a sense strand or antisense strand from which said suppression element is derived, and wherein said target gene of interest encodes a MBD1 or USP1 polypeptide, and wherein said plant exhibits delayed flowering time when compared to a control plant.

3. A transgenic plant (for example, a rice, maize or soybean plant) comprising in its genome a suppression DNA construct comprising at least one heterologous regulatory element operably linked to at least 100 contiguous base pairs of (a) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4 or 7, or (b) a full complement of the nucleic acid sequence of (a), and wherein said plant exhibits delayed flowering time when compared to a control plant.

4. The plant of embodiment 1 to 3, wherein the polynucleotide encodes a MBD1 or USP1 polypeptide, for example from *Oryza sativa, Oryza australiensis, Oryza barthii, Oryza glaberrima* (African rice), *Oryza latifolia, Oryza longistaminata, Oryza meridionalis, Oryza officinalis, Oryza punctata, Oryza rufipogon* (brownbeard or red rice), *Oryza nivara* (Indian wild rice), *Arabidopsis thaliana, Cicer arietinum, Solanum tuberosum, Brassica oleracea, Zea mays, Glycine max, Glycine tabacina, Glycine soja* or *Glycine tomentella*.

5. The plant of any one of embodiments 1 to 4, wherein the plant further comprises at least one polynucleotide encoding a flowering time-regulating polypeptide.

6. The plant of any one of embodiments 1 to 4, wherein the plant further comprises at least one recombinant polynucleotide encoding a polypeptide of interest.

7 Any progeny of the above plants in embodiments 1 to 6, any seeds of the above plants in embodiments 1 to 6, any seeds of progeny of the above plants in embodiments 1 to 6, and cells from any of the above plants in embodiments 1 to 6 and progeny thereof.

In any of the foregoing embodiments 1 to 7 or any other embodiments of the present disclosure, the recombinant DNA construct may comprise at least one heterologous promoter functional in a plant as a regulatory element.

The examples below describe some representative protocols and techniques for regulating plant flowering time and observing and/or evaluating plants agricultural characteristics under such conditions.

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct (i.e., the progeny not comprising the recombinant DNA construct is the control or reference plant).

2. Introgression of a recombinant DNA construct into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods

Methods include but are not limited to methods for regulating plant flowering time, methods for observing and/or evaluating plant agricultural characteristics, and methods for producing seed. The plant may be a monocotyledonous or dicotyledonous plant, for example, a rice, maize, *Arabidopsis*, soybean plant. The plant may also be sunflower, sorghum, canola, wheat, alfalfa, cotton, barley or millet. The seed may be a rice, maize, *Arabidopsis* or soybean seed, for example a maize hybrid seed or maize inbred seed.

Methods include but are not limited to the following:

A method for transforming a cell comprising transforming a cell with any of the isolated polynucleotides of the present disclosure. The cell transformed by this method is also included. In particular embodiments, the cell is eukaryotic cell, e.g., a yeast, insect or plant cell, or prokaryotic, e.g., a bacterium.

A method for producing a transgenic plant comprising transforming a plant cell with any of the isolated polynucleotides or recombinant DNA constructs of the present disclosure and regenerating a transgenic plant from the transformed plant cell. The disclosure is also directed to the transgenic plant produced by this method, and transgenic seed obtained from this transgenic plant.

A method for isolating a polypeptide of the disclosure from a cell or culture medium of the cell, wherein the cell comprises a recombinant DNA construct comprising a polynucleotide of the disclosure operably linked to at least one regulatory element, and wherein the transformed host cell is grown under conditions that are suitable for expression of the recombinant DNA construct.

A method of altering the level of expression of a polypeptide of the disclosure in a host cell comprising: (a) transforming a host cell with a recombinant DNA construct of the present disclosure; and (b) growing the transformed host cell under conditions that are suitable for expression of the recombinant DNA construct wherein expression of the recombinant DNA construct results in production of altered levels of the polypeptide of the disclosure in the transformed host cell.

A methods for increasing drought tolerance in a plant, comprising: (a) introducing into a regenerable plant cell a recombinant DNA construct comprising a polynucleotide operably linked to at least one heterologous regulatory sequence, wherein the polynucleotide encodes a polypeptide having an amino acid sequence of at least 80% sequence identity, when compared to SEQ ID NO: 4 or 7; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased drought tolerance when compared to a control plant not comprising the recombinant DNA construct, and the said improved drought tolerance may be increased survival rate, reduced leaf rolling degree, improved seed setting rate, or increased grain yield under drought condition.

A method of producing seed comprising any of the preceding methods, and further comprising obtaining seeds from said progeny plant, wherein said seeds comprise in their genome said recombinant DNA construct.

In some embodiments, the disclosure provides seeds that comprise in their genome the recombinant DNA construct of the disclosure The introduction of recombinant DNA constructs of the present disclosure into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation. Techniques for plant transformation and regeneration have been described in International Patent Publication WO 2009/006276, the contents of which are herein incorporated by reference.

In addition, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" engineered endonucleases such as meganucleases produced to modify plant genomes (e.g., WO 2009/114321; Gao et al. (2010) Plant Journal 1:176-187). Another site-directed engineering is through the use of zinc finger domain recognition coupled with the restriction properties of restriction enzyme (e.g., Urnov, et al. (2010) *Nat Rev Genet.* 11(9):636-46; Shukla, et al. (2009) *Nature* 459 (7245):437-41). A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326 (5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The CRISPR/Cas system allows targeted cleavage of genomic DNA guided by a customizable small noncoding RNA.

The development or regeneration of plants containing the foreign, exogenous isolated nucleic acid fragment that encodes a protein of interest is well known in the art. The regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

Stacking of Traits

Modified plants may comprise a stack of one or more flowering time-regulating polynucleotides disclosed herein with one or more additional polynucleotides resulting in the production or suppression of multiple polypeptide sequences. Modified plants comprising stacks of polynucleotide sequences can be obtained by either or both of traditional breeding methods or through genetic engineering methods. These methods include, but are not limited to, breeding individual lines each comprising a polynucleotide of interest, genome editing, transforming a transgenic plant comprising a gene disclosed herein with a subsequent gene and cotransformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Expression of the sequences can be driven by the same promoter or by different promoters. In certain cases, it may be desirable to introduce a transformation cassette that will suppress the expression of the polynucleotide of interest. This may be combined with any combination of other suppression cassettes or over-expression cassettes to generate the desired combination of traits in the plant. It is further recognized that polynucleotide sequences can be stacked at a desired genomic location using a site-specific recombination system.

EXAMPLES

Example 1

Flowering Time-Regulating Genes Cloning and Over-Expression Vector Construction

Primers were designed for cloning rice flowering time-regulating genes. The primers and the expected-lengths of the amplified genes are shown in Table 2.

OsMBD1 and OsUSP1 cDNA were cloned from pooled cDNA from leaf, stem and root tissues of Zhonghua 11 plant. The PCR reaction mixtures and PCR procedures are shown in Table 3 and Table 4.

TABLE 2

Primers for cloning rice flowering time-regulating genes

| Primer | Sequence | SEQ ID NO: | Gene name | Length of amplified fragment (bp) |
|---|---|---|---|---|
| gc-5303 | 5'-GAGTATGGCCTCAT CCCCGTCACC-3' | 8 | OsMBD1 | 696 |
| gc-5304 | 5'-CACACAGATCACAG AGACCGAACAGAC-3' | 9 | | |
| gc-6508 | 5'-GCGTGCGGAATCTGT AGTAAACTAGTAATC-3' | 10 | OsUSP1 | 929 |
| gc-6509 | 5'-CAGATTCGCCACCT GTTCCCTGTATAC-3' | 11 | | |

TABLE 3

PCR reaction mixture

| Reaction mix | 50 µL |
|---|---|
| Template | 1 µL |
| TOYOBO KOD-FX (1.0 U/µL) | 1 µL |
| 2 × PCR buffer for KOD-FX | 25 µL |
| 2 mM dNTPs (0.4 mM each) | 10 µL |
| Primer-F/R (10 µM) | 2 µL each |
| ddH$_2$O | 9 µL |

TABLE 4

PCR cycle conditions for cloning rice flowering time-regulating genes

| 94° C. | 3 min | |
| 98° C. | 10 s | |
| 58° C. | 30 s | ×30 |
| 68° C. | (1 Kb/min) min | |
| 68° C. | 5 min | |

The PCR amplified products were extracted after the agarose gel electrophoresis using a column kit and then ligated with TA cloning vectors. The sequence and orientation in the construct was confirmed by sequencing. The genes were cloned into plant binary construct DP0158 (pCAMBIA1300-DsRed) (SEQ ID NO: 1). The cloned nucleotide sequence in construct of DP0995 and coding sequence of OsMBD1 are provided as SEQ ID NO: 2 and 3, the encoded amino acid sequence of OsMBD1 is SEQ ID NO: 4. The cloned nucleotide sequence in construct of DP0998 and coding sequence of OsUSP1 are provided as SEQ ID NO: 5 and 6, the encoded amino acid sequence of OsUSP1 is SEQ ID NO: 7.

Example 2

Generation Rice Plants with Increased Gene Expression

The over-expression vectors and empty vectors (DP0158) were transformed into Zhonghua 11 (*Oryza sativa* L.) by Agrobacteria-mediated method as described by Lin and Zhang (*Plant Cell Rep.* 23: 540-547(2005)). The transgenic seedlings ($T_0$) generated in transformation laboratory were transplanted in the field to get $T_1$ seeds. The $T_1$ and $T_2$ seeds were stored at cold room (4° C.). The over-expression vectors contain DsRED and HYG genes. $T_1$ and $T_2$ seeds which showed red color under green fluorescent light were transgenic seeds and were used in the following early flowering assays.

Gene Expression Analysis in Transgenic Rice Plants:

Gene expression levels in the transgenic rice plants are analyzed by a standard real-time RT-PCR procedure, such as the QuantiTect® Reverse Transcription Kit from Qiagen® and Real-Time RT-PCR (SYBR$^R$Premix Ex Taq™, TaKaRa). EF1α gene is used as an internal control to show that the amplification and loading of samples from the transgenic rice and control plant are similar. The expression level is normalized based on the EF1α mRNA levels.

OsMBD1 gene expression levels in the DP0995 rice plants were detected using the following primers. mRNA was extracted from the top second leaf of $T_1$ generation seedlings which were at grain filling stage. As shown in FIG. 1, the expression level in ZH11-TC rice is set at 1.00, the gene expression level in ZH11-WT and DP0158 rice is similar to that of ZH11-TC, and OsMBD1 over-expressed in all the fifteen lines.

(SEQ ID NO: 12)
DP995-F1: 5'-CTGACTGCTCGTGTGAAGAC-3'

(SEQ ID NO: 13)
DP995-R1: 5'-TGGAGGCTTTGGTATGTTAGG-3'

Figure 2:
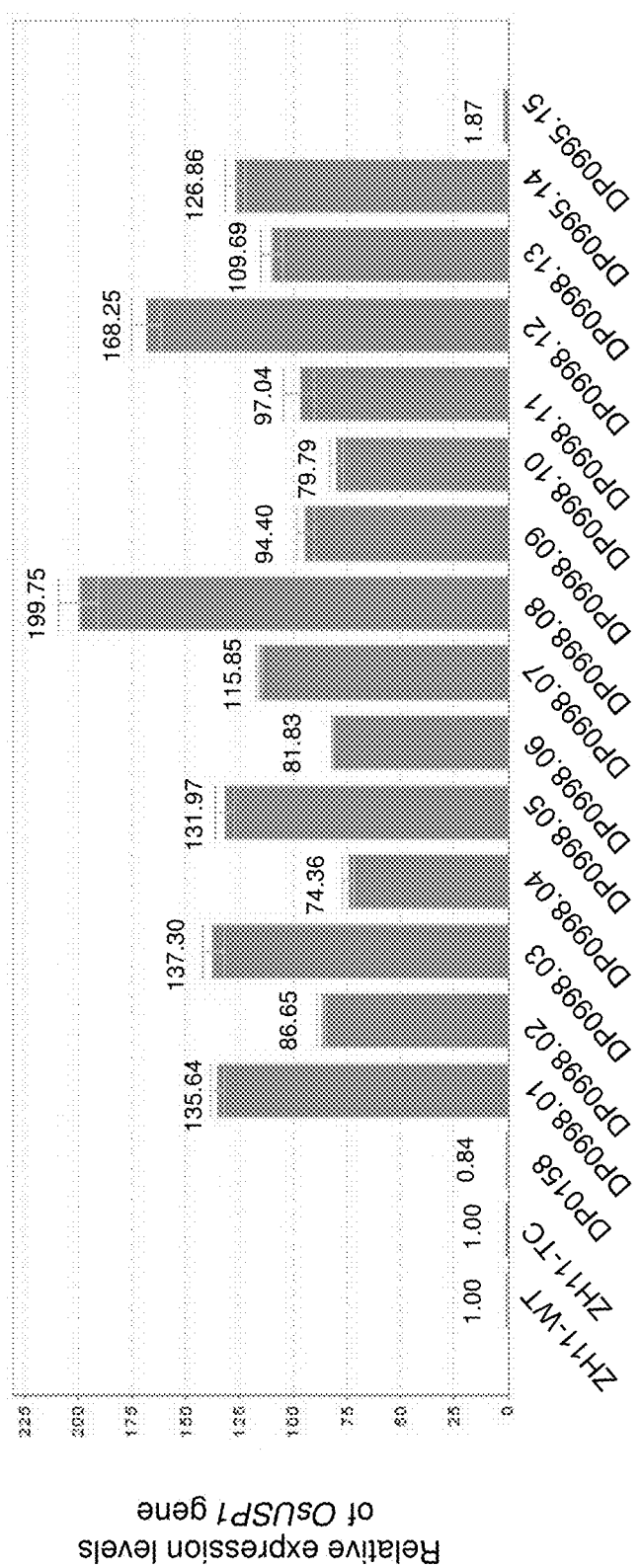

OsUSP1 gene expression levels in the DP0998 rice plants were detected using the primers shown as SEQ ID NO: 14 and 15. mRNA was extracted from the top second leaf of $T_1$ generation seedlings which were at grain filling stage. As shown in FIG. 2, the expression level in ZH11-TC rice is set at 1.00, the gene expression level in ZH11-WT and DP0158 rice is similar to that of ZH11-TC, and OsUSP1 over-expressed in fourteen lines, the expression level of OsUSP1 gene in DP0998.15 line is only 1.87 times that in ZH11-TC, which was much lower than that in other transgenic lines.

(SEQ ID NO: 14)
DP0998-F1: 5'-CCCTACAAGATCCACATCGTC-3'

(SEQ ID NO: 15)
DP0998-R1: 5'-CTTCCAAGCCTCCCCTTG-3'

Example 3

Flowering Trait Observation for the OsMBD1 Transgenic Rice

The $T_1$ generation OsMBD1 transgenic plants were propagated in Beijing field (40° 13'N, 116° 13'E) to get $T_2$ seeds. The phenotype was recorded during the plant growth.
Method:

$T_1$ transgenic seeds were sterilized by 800 ppm carbendazol for 8 h at 32° C. and washed 3~5 times with distilled water, then soaked in water for 16 h at 32° C., germinated for 18 h at 35~37° C. in an incubator. The germinated seeds were planted in a seedbed field, and at 3-leaf stage, the seedlings were transplanted into Beijing field. Ten plants from each transgenic line were planted in one row, and ZH11-WT (Zhonghua 11 wild type), ZH11-TC (tissue cultured Zhonghua 11) and DP0158 (transformed with empty vector DP0158) were planted nearby the transgenic lines in the same block, and were used as controls.

The rice plants were managed by normal practice using pesticides and fertilizers. Plant phenotypes were observed and recorded during the experiments.

Heading date and maturity date were recorded. The heading date is the date when 50% young panicles head out the sheath of flag leaf for one plant in one row. The maturity date is the date when 90% glume, grain spikelet axis or vice glume become yellow from appearance, which is the best harvest period. If the heading date of the transgenic rice plants are earlier than that of the control plants (Zhonghua 11, ZH11-TC or DP0158 plants), the transgenic rice line was thought to be early heading plants and the gene play a role in regulating the flowering time of plants.

The plant height, effective panicle number and grain yield per plant were measured. The plant height is the length from the surface of the field to the top of the highest panicle or leaf and was measure before harvest. At the end of the season, all or about six representative plants of each transgenic line were harvested from the middle of the row per line. The panicles first were cut and store in one bag, and then the stems were cut above the earth and put in another bag. The effective panicle number per plant was obtained by counting, and the grain yield per plant was measured. The plant height, effective panicle number and grain yield data were statistically analyzed using mixed linear model by ASRemI program.
Results:

Fifteen OsMBD1 transgenic rice lines were sowed and transplanted into Beijing field. The rice plants were managed by normal practice. On August 6, 12 tested rice lines exhibited 50% young panicles out the sheath of the flag leaf; seven of the ten DP0995.03 rice plants and eight of the ten DP0995.07 rice plants exhibited 50% young panicles. A half of the DP0995.12 rice plants have been heading (50% young panicles) on August 6 and half rice plants have been heading on August 10. While the control plants: ZH11-WT, ZH11-TC and DP0158 plants exhibited 50% young panicles on August 21. These results mean almost all the transgenic rice lines have been heading earlier than the control plants for about 15 days. The transgenic rice plants also matured earlier than the controls for about 15 days.

TABLE 5

Flowering trait, plant height and grain yield of OsMBD1 transgenic rice plants at $T_1$ generation in Beijing

| Line ID | Days to heading date (d) | Diff of heading date | Days to maturity date (d) | Plant height (cm) | Effective panicle number per plant | Average grain yield per plant (g) |
|---|---|---|---|---|---|---|
| ZH11-WT | 101 | 0 | 147 | 132.48 | 11.60 | 46.80 |
| ZH11-TC | 101 | / | 147 | 132.64 | 9.32 | 41.05 |
| DP0158 | 101 | 0 | 147 | 130.32 | 11.40 | 40.78 |
| DP0995.01 | 86 | 15 | 132 | 123.85 | 10.72 | 42.89 |
| DP0995.02 | 86 | 15 | 132 | 128.44 | 11.71 | 42.72 |
| DP0995.03 | 86 | 15 (7/10) | 132 | 128.95 | 10.52 | 45.40 |
| DP0995.05 | 86 | 15 | 132 | 123.00 | 10.32 | 41.90 |
| DP0995.06 | 86 | 15 | 132 | 125.89 | 11.61 | 49.23 |
| DP0995.07 | 86 | 15 (8/10) | 132 | 120.62 | 11.41 | 51.01 |
| DP0995.08 | 86 | 15 | 132 | 126.06 | 13.98 | 58.92 |
| DP0995.09 | 86 | 15 | 132 | 124.53 | 11.71 | 44.97 |
| DP0995.10 | 86 | 15 | 132 | 133.54 | 11.31 | 47.51 |
| DP0995.11 | 86 | 15 | 132 | 129.80 | 11.41 | 45.17 |
| DP0995.12 | 86 | 15 (5/10), 11 (5/10) | 132 | 124.19 | 10.82 | 44.62 |
| DP0995.13 | 86 | 15 | 132 | 129.80 | 10.23 | 43.88 |
| DP0995.14 | 86 | 15 | 132 | 125.89 | 10.23 | 40.12 |
| DP0995.15 | 86 | 15 | 132 | 123.68 | 10.82 | 42.59 |
| DP0995.16 | 86 | 15 | 132 | 127.76 | 11.61 | 43.76 |

Heading date or flowering time plays an important role in regulating the biomass of crops by affecting their duration of basic vegetative growth and thereby grain yield, to further substantiate this notion, the plant height, effective panicle number and grain yield were measured. Table 6, 7 and 8 shows that the average grain yield per plant of OsMBD1 transgenic rice plants were lower than that of ZH11-WT, but greater than that of both ZH11-TC and DP0158 controls and the differences were not reach significant level; the OsMBD1 transgenic rice plants were significantly shorter than ZH11-WT, ZH11-TC and DP0158 control plants; and there was no significant difference for the effective panicle number for the transgenic and control plants.

TABLE 6

Grain yield analysis of OsMBD1 transgenic rice plants at $T_1$ generation and at construct level

| Line ID | Grain yield per plant (g) | CK = ZH11-WT | | | CK = ZH11-TC | | | CK = DP0158 | | |
|---|---|---|---|---|---|---|---|---|---|---|
| | | Diff | P value | P ≤ 0.1 | Diff | P value | P ≤ 0.1 | Diff | P value | P ≤ 0.1 |
| ZH11-WT | 46.80 | | | | | | | | | |
| ZH11-TC | 41.05 | | | | | | | | | |
| DP0158 | 40.78 | | | | | | | | | |
| DP0995 | 45.65 | −1.15 | 0.894 | | 4.59 | 0.594 | | 4.87 | 0.573 | |

TABLE 7

Plant height analysis of OsMBD1 transgenic rice plants at $T_1$ generation and at construct level

| Line ID | Plant height (cm) | CK = ZH11-WT | | | CK = ZH11-TC | | | CK = DP0158 | | |
|---|---|---|---|---|---|---|---|---|---|---|
| | | Diff | P value | P ≤ 0.1 | Diff | P value | P ≤ 0.1 | Diff | P value | P ≤ 0.1 |
| ZH11-WT | 132.48 | | | | | | | | | |
| ZH11-TC | 132.64 | | | | | | | | | |
| DP0158 | 130.32 | | | | | | | | | |
| DP0995 | 126.40 | −6.08 | 0.000 | Y | −6.24 | 0.016 | Y | −3.92 | 0.001 | Y |

TABLE 8

Effective panicle number analysis of OsMBD1 transgenic rice plants at $T_1$ generation and at construct level

| Line ID | Effect panicle number | CK = ZH11-WT | | | CK = ZH11-TC | | | CK = DP0158 | | |
|---|---|---|---|---|---|---|---|---|---|---|
| | | Diff | P value | P ≤ 0.1 | Diff | P value | P ≤ 0.1 | Diff | P value | P ≤ 0.1 |
| ZH11-WT | 11.60 | | | | | | | | | |
| ZH11-TC | 9.32 | | | | | | | | | |

TABLE 8-continued

Effective panicle number analysis of OsMBD1 transgenic rice plants at $T_1$ generation and at construct level

| Line ID | Effect panicle number | CK = ZH11-WT | | | CK = ZH11-TC | | | CK = DP0158 | | |
|---|---|---|---|---|---|---|---|---|---|---|
| | | Diff | P value | P ≤ 0.1 | Diff | P value | P ≤ 0.1 | Diff | P value | P ≤ 0.1 |
| DP0158 | 11.40 | | | | | | | | | |
| DP0995 | 11.23 | −0.37 | 0.631 | | 1.91 | 0.015 | Y | −0.17 | 0.824 | |

When obtained the $T_2$ seeds, we measured the fluorescent ratio of $T_2$ seeds under green fluorescent lamps. Analysis of the obtained $T_2$ seeds showed a 3:1 segregation ratio of fluorescent and non-fluorescent seeds, indicating that these transgenic individual plants contained a single copy of OsMBD1 gene.

Example 4

Flowering Trait Validation of OsMBD1 Transgenic Rice

Heading date or flowering time is an important agronomic trait, which plays a key role in the adaptation and geographic distribution of rice varieties. Appropriate heading date is a prerequisite for attaining the desired yield level.

To further investigate the flowering trait of OsMBD1 transgenic rice plants and to investigate whether the temperature or photoperiod affect the heading date or flowering time in rice, $T_1$ and $T_2$ seeds were planted in different locations or environments: HN (Hainan, 18° 30'N, 109° 3'E), BJ (Beijing, 40° 13'N, 116° 13'E) and NX (Ningxia, 38° 36'N, 106° 23'E, altitude 1106.3 m).

The experiment method is same to that described in Example 3.

Results:

$T_1$ Generation Plants 1) 2015 HN

Six $T_1$ OsMBD1 transgenic rice plants were planted and the ZH11-TC was used as control. These plants were sowed on November 21, and transplanted in the paddy field on December 15. The days from sowing to heading date for the ZH11-TC control was 84 days, four transgenic lines exhibited the same heading date as the ZH11-TC control, and only two lines showed three days earlier heading date. There was no difference for maturity date between the earlier heading rice lines and the other four transgenic rice lines. These rice plants matured at the same time.

Table 9 shows the average grain yield of per plant. The two earlier heading lines showed less grain yield per plant than ZH11-TC control, and other lines showed greater grain yield per plant than ZH11-TC control.

TABLE 9

Flowering trait and grain yield analysis of OsMBD1 transgenic rice at $T_1$ generation in Hainan

| Line ID | Days to heading date (d) | Diff of heading date | Days to maturity date (d) | Average grain yield per plant (g) |
|---|---|---|---|---|
| ZH11-TC | 84 | / | 126 | 10.86 |
| DP0995.05 | 81 | 3 | 126 | 9.07 |
| DP0995.06 | 81 | 3 | 126 | 9.63 |
| DP0995.07 | 84 | 0 | 126 | 11.75 |

TABLE 9-continued

Flowering trait and grain yield analysis of OsMBD1 transgenic rice at $T_1$ generation in Hainan

| Line ID | Days to heading date (d) | Diff of heading date | Days to maturity date (d) | Average grain yield per plant (g) |
|---|---|---|---|---|
| DP0995.08 | 84 | 0 | 126 | 13.70 |
| DP0995.11 | 84 | 0 | 126 | 12.02 |
| DP0995.16 | 84 | 0 | 126 | 10.99 |

2) 2015 BJ

Six OsMBD1 transgenic rice lines were planted in Beijing paddy field, and ZH11-TC, DP0158 and DP0995.BN ($T_2$ non-fluorescent seeds segregated from the $T_2$ DP0995 transgenic seeds) were used as controls. The $T_1$ transgenic seeds and the control seeds were sowed on April 22, which was earlier than the sowing date in Beijing in previous year. 91 days after sowing, 50% young panicle of DP0995.15 rice plants headed out the sheath of the flag leaf, and other five transgenic rice lines also exhibited earlier heading date (Table 10). These results confirmed the earlier heading trait of the OsMBD1 transgenic rice plants and demonstrated that the OsMBD1 transgenic rice plants headed earlier than the controls for 9~14 days.

As shown in Table 10, all the six OsMBD1 transgenic rice lines were shorter than the controls; the panicle number of OsMBD1 transgenic rice plants were less than ZH11-TC, but no difference from that of DP0158 and DP0995.BN; and the transgenic rice plants exhibited less grain yield per plant than the control plants.

TABLE 10

Flowering trait, plant height and grain yield analysis of OsMBD1 transgenic rice plant at $T_1$ generation in Beijing ($2^{nd}$ experiment)

| Line ID | Days to heading date (d) | Diff of heading date | Days to maturity date (d) | Plant height (cm) | Effective panicle number per plant | Average grain yield per plant (g) |
|---|---|---|---|---|---|---|
| ZH11-TC | 105 | / | 151 | 129.25 | 12.5 | 43.05 |
| DP0158 | 105 | 0 | 151 | 133.17 | 11.4 | 30.29 |
| DP0995.BN | 105 | 0 | 151 | 127.67 | 11.0 | 40.57 |
| DP0995.02 | 94 | 11 | 141 | 117.69 | 10.3 | 37.10 |
| DP0995.03 | 96 | 9 | 141 | 124.82 | 12.0 | 45.45 |
| DP0995.08 | 93 | 12 | 141 | 112.99 | 10.3 | 34.61 |
| DP0995.10 | 93 | 12 | 141 | 118.90 | 10.9 | 37.62 |
| DP0995.12 | 95 | 10 | 141 | 113.90 | 10.9 | 38.99 |
| DP0995.15 | 91 | 14 | 138 | 110.10 | 11.2 | 36.79 |

3) 2015 NX

The same six OsMBD1 transgenic rice lines planted in Beijing were test in Ningxia, and ZH11-TC and DP0158 seedling were used as controls. These seeds were sowed on April 14, and transplanted in field on May 18.108 days after sowing, 50% young panicle of DP0995.15 headed out the sheath of flag leaf, and 50% young panicles of ZH11-TC and DP0158 rice plants headed out 128 days after sowing. Compared to ZH11-TC and DP0158 plants, the OsMBD1 transgenic rice showed 1320 earlier heading date (Table 11).

Further analysis indicates that the OsMBD1 transgenic rice plants were taller than both the controls, and exhibited more effective panicle number. OsMBD1 transgenic rice plants matured at September, while ZH11-TC and DP0158 rice plants were not fully mature because of low temperature at early October. The average grain yield per plant of OsMBD1 transgenic rice plants were greater than that of ZH11-TC and DP0158 plants.

TABLE 11

Flowering trait, plant height and grain yield analysis of OsMBD1 transgenic rice plants at $T_1$ generation in Ningxia

| Line ID | Days to heading date (d) | Diff of heading date | Days to maturity date (d) | Plant height (cm) | Effective panicle number per plant | Average grain yield per plant (g) |
|---|---|---|---|---|---|---|
| ZH11-TC | 128 | / | 174 | 88.95 | 15.13 | 10.56 |
| DP0158 | 128 | 0 | 174 | 82.33 | 12.17 | 4.99 |
| DP0995.02 | 109 | 19 | 155 | 98.65 | 15.57 | 28.82 |
| DP0995.03 | 115 | 13 | 167 | 98.17 | 16.39 | 41.29 |
| DP0995.08 | 109 | 19 | 155 | 99.45 | 16.04 | 40.28 |
| DP0995.10 | 109 | 19 | 155 | 105.91 | 15.45 | 38.76 |
| DP0995.12 | 110 | 18 | 155 | 96.09 | 15.33 | 28.49 |
| DP0995.15 | 108 | 20 | 155 | 103.60 | 18.87 | 39.76 |

$T_2$ Generation Plants
1) 2015 HN

Seeds from nine different plants of seven transgenic lines were planted in Hainan, and ZH11-TC rice plants were used as control. DP0995.12 rice plants showed seven days earlier heading date than ZH11-TC plants and other transgenic plants have similar heading date as the ZH11-TC plants. The grain yield per plant of the earlier heading lines were less than that of ZH11-TC, however the grain yield per plant of OsMBD1 transgenic rice plants is same to that of ZH11-TC at the construct level.

TABLE 12

Flowering trait and grain yield analysis of OsMBD1 transgenic rice at $T_2$ generation in Hainan

| Line ID | Days to heading date (d) | Diff of heading date | Days to maturity date (d) | Average grain yield per plant (g) |
|---|---|---|---|---|
| ZH11-TC | 84 | / | 126 | 9.78 |
| DP0995.03.02 | 84 | 0 | 126 | 9.77 |
| DP0995.03.03 | 87 | −3 | 131 | 11.58 |
| DP0995.05.01 | 83 | 0 | 126 | 7.79 |
| DP0995.06.01 | 85 | 0 | 126 | 9.75 |
| DP0995.08.06 | 85 | 0 | 126 | 10.69 |
| DP0995.11.01 | 85 | 0 | 126 | 10.89 |
| DP0995.12.02 | 77 | 7 | 121 | 8.60 |
| DP0995.12.04 | 77 | 7 | 121 | 7.49 |
| DP0995.16.02 | 85 | 0 | 126 | 11.62 |

2) 2015 BJ

The $T_2$ seeds were planted in Beijing field for two times. The sowing date of the first experiment is earlier than that in the previous year and the sowing date of the second experiment is similar to that in the previous year. The same OsMBD1 transgenic lines were planted and ZH11-TC, DP0158 and DP0995.BN rice plants were used as control and planted near the transgenic rice plants.

As shown in Table 13 and 14, The twelve transgenic rice lines showed 8~14 days earlier heading date than the controls except DP0995.03.61 rice plants in the first experiment and showed 5~11 days earlier heading date than controls except DP0995.03.61 and DP0995.03.62 rice plants. These results further demonstrate that $T_1$ and $T_2$ OsMBD1 transgenic rice plants showed earlier heading trait in Beijing field.

Further analysis shows that the OsMBD1 transgenic rice plants were shorter than the controls plants in two experiments. There were no remarkable different for the effective panicle number. The average grain yield per plant of OsMBD1 transgenic rice was less than that of ZH11-TC controls in two experiments.

TABLE 13

Flowering trait, plant height and grain yield analysis of OsMBD1 transgenic rice plants at $T_2$ generation in Beijing (1st experiment)

| Line ID | Days to heading date (d) | Diff of heading date | Days to maturity date (d) | Plant height (cm) | Effective panicle number per plant | Average grain yield per plant (g) |
|---|---|---|---|---|---|---|
| ZH11-TC | 105 | / | 151 | 129.25 | 12.5 | 43.05 |
| DP0158 | 105 | 0 | 151 | 133.17 | 11.4 | 30.29 |
| DP0995.BN | 105 | 0 | 151 | 127.67 | 11.0 | 40.57 |
| DP0995.02.64 | 91 | 14 | 138 | 100.70 | 10.8 | 22.99 |
| DP0995.02.65 | 91 | 14 | 138 | 106.16 | 12.5 | 29.77 |
| DP0995.03.61 | 108 | −3 | 153 | 130.62 | 14.0 | 65.19 |
| DP0995.03.62 | 94 | 11 | 141 | 113.14 | 10.8 | 35.41 |
| DP0995.08.61 | 91 | 14 | 138 | 112.33 | 9.3 | 27.98 |
| DP0995.08.64 | 91 | 14 | 138 | 113.29 | 9.9 | 31.00 |
| DP0995.10.64 | 91 | 14 | 138 | 112.98 | 10.7 | 29.41 |
| DP0995.10.65 | 92 | 13 | 138 | 108.51 | 11.1 | 33.25 |
| DP0995.12.61 | 97 | 8 | 141 | 124.52 | 10.6 | 40.33 |
| DP0995.12.62 | 95 | 10 | 141 | 112.99 | 11.1 | 33.65 |
| DP0995.15.69 | 91 | 14 | 138 | 94.02 | 10.6 | 21.44 |
| DP0995.15.70 | 91 | 14 | 138 | 103.58 | 10.0 | 22.31 |

TABLE 14

Flowering trait, plant height and grain yield analysis of OsMBD1 transgenic tice plants at $T_2$ generation in Beijing (2nd experiment)

| Line ID | Days to heading date (d) | Diff of heading date | Days to maturity date (d) | Plant height (cm) | Effective panicle number per plant | Average grain yield per plant (g) |
|---|---|---|---|---|---|---|
| ZH11-TC | 96 | / | 139 | 133.67 | 8.77 | 56.74 |
| DP0158 | 96 | 0 | 139 | 135.83 | 10.17 | |
| DP0995.BN | 96 | 0 | 139 | 134.33 | 11.33 | 39.00 |
| DP0995.02.65 | 87 | 9 | 130 | 121.13 | 10.02 | 32.49 |
| DP0995.03.61 | 96 | 0 | 138 | 118.43 | 11.20 | 34.67 |
| DP0995.03.62 | 96 | 0 | 139 | 131.35 | 11.20 | 26.54 |
| DP0995.08.61 | 87 | 9 | 130 | 121.13 | 10.02 | 39.93 |
| DP0995.08.64 | 87 | 9 | 130 | 122.93 | 11.20 | 41.27 |
| DP0995.10.64 | 85 | 11 | 130 | 122.33 | 10.61 | 38.83 |
| DP0995.10.65 | 87 | 9 | 130 | 127.44 | 12.39 | 47.06 |
| DP0995.12.61 | 91 | 5 | 134 | 125.04 | 9.57 | 35.21 |
| DP0995.12.62 | 91 | 5 | 134 | 122.63 | 11.05 | 40.33 |
| DP0995.15.69 | 85 | 11 | 130 | 115.42 | 10.91 | 34.28 |
| DP0995.15.70 | 87 | 9 | 130 | 115.87 | 9.13 | 31.12 |

3) 2015 NX

T$_2$ OsMBD1 seeds from twelve plants of six transgenic lines were planted in Ningxia, and ZH11-TC and DP0158 plants were used as controls. 50% young panicle of ZH11-TC and DP0158 plants headed out 128 d after sowing, and the transgenic rice plants showed 18~23 days earlier heading date than the control plants except DP0995.03.61 rice plants. The transgenic rice plants matured earlier than the ZH11-TC and DP0158 plant.

The plant height and the grain yield were measured, and were shown in Table 15. Most the OsMBD1 transgenic rice plants were taller and had greater grain yield than the ZH11-TC and DP0158 plants. The grain yield of ZH11-TC and DP0158 controls were less because of cold temperature and later heading of the ZH11-TC and DP0158 plants. Earlier heading date or flowering time was useful for avoiding frost or low temperature in the later maturity stage.

TABLE 15

Flowering trait, plant height and grain yield analysis of OsMBD1 transgenic rice at T$_2$ generation in Ningxia

| Line ID | Days to heading date (d) | Diff of heading date | Days to maturity date (d) | Plant height (cm) | Effective panicle number per plant | Average grain yield per plant (g) |
| --- | --- | --- | --- | --- | --- | --- |
| ZH11-TC | 128 | / | 174 | 88.95 | 15.13 | 10.56 |
| DP0158 | 128 | 0 | 174 | 82.33 | 12.17 | 4.99 |
| DP0995.02.64 | 107 | 21 | 151 | 91.51 | 14.15 | 30.58 |
| DP0995.02.65 | 108 | 20 | 152 | 88.05 | 12.97 | 21.74 |
| DP0995.03.61 | 128 | 0 | 174 | 72.47 | 13.56 | 2.78 |
| DP0995.03.62 | 108 | 20 | 151 | 90.09 | 14.03 | 30.62 |
| DP0995.08.61 | 110 | 18 | 155 | 96.45 | 16.86 | 32.10 |
| DP0995.08.64 | 110 | 18 | 155 | 97.13 | 14.50 | 25.97 |
| DP0995.10.64 | 110 | 18 | 155 | 96.92 | 15.33 | 23.63 |
| DP0995.10.65 | 110 | 18 | 167 | 95.94 | 17.10 | 30.48 |
| DP0995.12.61 | 110 | 18 | 155 | 93.62 | 14.74 | 33.83 |
| DP0995.12.62 | 110 | 18 | 155 | 92.98 | 14.98 | 33.03 |
| DP0995.15.69 | 105 | 23 | 151 | 90.35 | 10.73 | 24.30 |
| DP0995.15.70 | 105 | 23 | 151 | 92.98 | 11.91 | 23.61 |

Example 5

Field Drought Test for OsMBD1 Transgenic Rice Plants

Flowering stage drought stress is an important problem in agriculture practice. The transgenic rice plants were further tested under field drought conditions. For the Field drought assays of mature rice plants, 12 transgenic lines from each gene construct were tested. The T$_2$ seeds were first sterilized as described in Example 3. The germinated seeds were planted in a seedbed field. At 3-leaf stage, the seedlings were transplanted into the testing field, with 4 replicates and 10 plants per replicate for each transgenic line, and the 4 replicates were planted in the same block. ZH11-TC, DP0158 and Bulk Null were planted nearby the transgenic lines in the same block, and were used as controls in the statistical analysis.

The rice plants were managed by normal practice using pesticides and fertilizers. Watering was stopped at the panicle initiation stage, so as to give drought stress at flowering stage, which also depends on the weather conditions (temperature and humidity). The soil water content was measured every 4 days at about 10 sites per block using TDR30 (Spectrum Technologies, Inc.).

Plant phenotypes were observed and recorded during the experiments. The phenotypes include heading date, leaf rolling degree, drought sensitivity and drought tolerance. Special attention was paid to leaf rolling degree at noontime. At the end of the growing season, six representative plants of each transgenic line were harvested from the middle of the row per line, and grain weight per plant was measured. The grain weight data were statistically analyzed using mixed linear model. Positive transgenic lines were selected based on the analysis (P<0.1).

Figure 3:
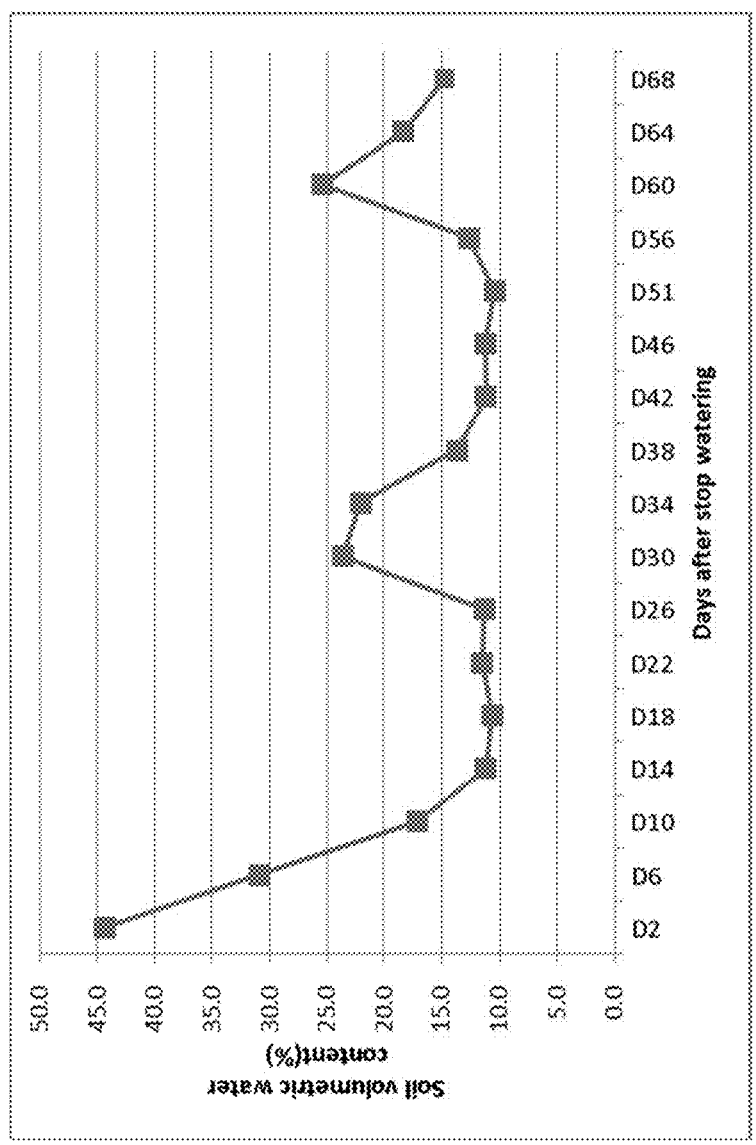
FIG. 3 shows changes of soil volumetric moisture content at different developmental stage in Ningxia field for drought testing OsMBD1 transgenic rice. The OsMBD1 transgenic rice started heading at 20 days after stopping watering and ZH11-TC rice plants started heading at 43 d after stopping watering.

Field Drought Assay Results:

Twelve OsMBD1 transgenic lines were tested in Ningxia Province. ZH11-TC, DP0158 and DP0995.BN planted nearby were used as controls. Watering was stopped from panicle initiation stage II of ZH11-TC rice plants to seed maturity to produce drought stress. The soil volumetric water content decreased from 45% to 10% before heading stage of OsMBD1 transgenic rice plants, two rainfalls after the heading stage of OsMBD1 transgenic rice and ZH11-TC rice plants increased the water content (FIG. 3). The OsMBD1 transgenic rice plants showed heading date earlier for about 23 days than the controls except DP0995.03.61, DP0995.06.61 and DP0995.09.69 transgenic lines, and DP0995.03.61 headed later than these controls for about seven days. The earlier headed transgenic rice plants matured earlier than controls, and were fully mature, while the control plants, DP0995.03.61, DP0995.06.61 and DP0995.09.69 rice plants were not fully mature because of cold temperature in the later stage. The OsMBD1 transgenic rice plants suffered a shorter time drought stress because of earlier heading and mature. As shown in Table 16, eleven lines obtained greater grain yields per plant than all the three controls. These results demonstrate that OsMBD1 rice plant had greater grain yield per plant than control after drought stress.

TABLE 16

Grain yield analysis of OsMBD1 transgenic rice plants under field drought conditions (1$^{st}$ experiment)

| Line ID | Number of survival plants | Number of harvested plants | Diff of heading date | Yield per plant (g) | CK = ZH11-TC | | | CK = DP0158 | | | CK = DP0995.BN | | |
| --- | --- | --- | --- | --- | --- | --- | --- | --- | --- | --- | --- | --- | --- |
| | | | | | Diff | P value | P ≤ 0.1 | Diff | P value | P ≤ 0.1 | Diff | P value | P ≤ 0.1 |
| DP0995 (construct) | | | | 14.71 | 10.82 | 0.000 | Y | 12.77 | 0.000 | Y | 12.04 | 0.000 | Y |
| ZH11-TC | 38 | 24 | / | 3.90 | | | | | | | | | |
| DP0158 | 37 | 22 | 0 | 1.94 | | | | | | | | | |
| DP0995.BN | 27 | 20 | 0 | 2.67 | | | | | | | | | |
| DP0995.01.63 | 38 | 23 | 23 | 17.58 | 13.68 | 0.000 | Y | 15.64 | 0.000 | Y | 14.91 | 0.000 | Y |
| DP0995.02.64 | 39 | 24 | 23 | 16.69 | 12.79 | 0.000 | Y | 14.74 | 0.000 | Y | 14.02 | 0.000 | Y |
| DP0995.03.61 | 39 | 18 | −7 | 2.40 | −1.50 | 0.097 | | 0.45 | 0.618 | | −0.28 | 0.760 | |
| DP0995.05.61 | 41 | 24 | 23 | 15.59 | 11.70 | 0.000 | Y | 13.65 | 0.000 | Y | 12.92 | 0.000 | Y |

TABLE 16-continued

Grain yield analysis of OsMBD1 transgenic rice plants under field drought conditions (1st experiment)

| Line ID | Number of survival plants | Number of harvested plants | Diff of heading date | Yield per plant (g) | CK = ZH11-TC | | | CK = DP0158 | | | CK = DP0995.BN | | |
|---|---|---|---|---|---|---|---|---|---|---|---|---|---|
| | | | | | Diff | P value | P ≤ 0.1 | Diff | P value | P ≤ 0.1 | Diff | P value | P ≤ 0.1 |
| DP0995.06.61 | 36 | 22 | 0 | 10.53 | 6.64 | 0.000 | Y | 8.59 | 0.000 | Y | 7.86 | 0.000 | Y |
| DP0995.09.69 | 38 | 23 | 0 | 5.16 | 1.27 | 0.133 | | 3.22 | 0.000 | Y | 2.49 | 0.003 | Y |
| DP0995.10.64 | 39 | 23 | 23 | 20.58 | 16.68 | 0.000 | Y | 18.63 | 0.000 | Y | 17.90 | 0.000 | Y |
| DP0995.12.62 | 35 | 25 | 23 | 14.97 | 11.08 | 0.000 | Y | 13.03 | 0.000 | Y | 12.30 | 0.000 | Y |
| DP0995.13.61 | 41 | 24 | 23 | 19.51 | 15.62 | 0.000 | Y | 17.57 | 0.000 | Y | 16.84 | 0.000 | Y |
| DP0995.14.65 | 40 | 24 | 23 | 16.57 | 12.68 | 0.000 | Y | 14.63 | 0.000 | Y | 13.90 | 0.000 | Y |
| DP0995.15.67 | 38 | 23 | 23 | 13.18 | 9.28 | 0.000 | Y | 11.23 | 0.000 | Y | 10.51 | 0.000 | Y |
| DP0995.16.61 | 39 | 24 | 23 | 23.80 | 19.90 | 0.000 | Y | 21.85 | 0.000 | Y | 21.12 | 0.000 | Y |

Twelve OsMBD1 transgenic lines were tested again in Ningxia Province. ZH11-TC, DP0158 and DP0995.BN planted nearby were used as controls. Watering was stopped from panicle initiation stage II of ZH11-TC rice plants to seed maturity to produce drought stress. The soil volumetric water content decreased from 60% to 20% before heading stage of OsMBD1 transgenic rice plants, one rainfall after the heading stage of OsMBD1 transgenic rice and ZH11-TC rice plants increased the water content. The OsMBD1 transgenic rice plants showed heading date earlier for about 27 days than the controls. The earlier headed transgenic rice plants matured earlier than controls, and were fully mature, and the control plants were fully mature at the early October. The OsMBD1 transgenic rice plants suffered a shorter time drought stress because of earlier heading and mature. As shown in Table 17, all the earlier headed lines obtained greater grain yields per plant than all the three controls. These results demonstrate that OsMBD1 rice plant had greater grain yield per plant than control after drought stress.

TABLE 17

Grain yield analysis of OsMBD1 transgenic rice plants under field drought conditions (2nd experiment)

| Line ID | Number of survival plants | Number of harvested plants | Yield per plant (g) | CK = ZH11-TC | | | CK = DP0158 | | | CK = DP0995.BN | | |
|---|---|---|---|---|---|---|---|---|---|---|---|---|
| | | | | Diff | P value | P ≤ 0.1 | Diff | P value | P ≤ 0.1 | Diff | P value | P ≤ 0.1 |
| DP0995 (Construct) | 437 | 264 | 14.44 | 9.04 | 0.000 | Y | 9.78 | 0.000 | Y | 8.91 | 0.000 | Y |
| ZH11-TC | 40 | 24 | 5.40 | | | | | | | | | |
| DP0158 | 39 | 24 | 4.66 | | | | | | | | | |
| DP0995.BN | 39 | 24 | 5.53 | | | | | | | | | |
| DP0995.01 | 40 | 24 | 17.09 | 11.69 | 0.000 | Y | 12.43 | 0.000 | Y | 11.56 | 0.000 | Y |
| DP0995.02 | 39 | 24 | 14.78 | 9.38 | 0.000 | Y | 10.13 | 0.000 | Y | 9.25 | 0.000 | Y |
| DP0995.05 | 40 | 24 | 12.74 | 7.34 | 0.000 | Y | 8.08 | 0.000 | Y | 7.21 | 0.000 | Y |
| DP0995.10 | 40 | 24 | 13.71 | 8.31 | 0.000 | Y | 9.05 | 0.000 | Y | 8.18 | 0.000 | Y |
| DP0995.13 | 40 | 24 | 14.25 | 8.85 | 0.000 | Y | 9.60 | 0.000 | Y | 8.72 | 0.000 | Y |
| DP0995.14 | 40 | 24 | 11.65 | 6.25 | 0.000 | Y | 6.99 | 0.000 | Y | 6.12 | 0.000 | Y |
| DP0995.15 | 40 | 24 | 16.57 | 11.17 | 0.000 | Y | 11.91 | 0.000 | Y | 11.04 | 0.000 | Y |
| DP0995.16 | 40 | 24 | 14.72 | 9.31 | 0.000 | Y | 10.06 | 0.000 | Y | 9.18 | 0.000 | Y |

Example 6

Flowering Trait Observation for the OsUSP1 Transgenic Rice Plant

The $T_1$ generation OsUSP1 transgenic seeds were propagated in Beijing field (40° 13'N, 116° 13'E) to obtain $T_2$ seeds. The phenotype was recorded during the experiment. The experimental method is same to that described in Example 3.

Results:

Fifteen OsUSP1 transgenic rice lines were sowed on May 12 and transplanted into Beijing field on June 12. The rice plants were irrigated and managed by normal practice. Plant phenotypes were recorded. Fourteen lines exhibited 50% young panicles headed out the sheath of the flag leaf on August 4; only one transgenic rice line DP0998.15 exhibited 50% young panicles headed on August 16; and the three controls headed normally on August 21. Fourteen transgenic lines showed 17 days earlier heading date than the controls and these fourteen transgenic lines exhibited higher relative expression level of OsUSP1 gene. DP0998.15 line showed only five days earlier heading date and showed a little lower relative gene expression level. We speculated that the earlier heading days is correlated to the relative expression levels of OsUSP1 gene in different transgenic lines (FIG. 2). These results clearly show that the OsUSP1 transgenic rice plants is earlier heading plants and OsUSP1 may play an important role in regulating flowering time.

The OsUSP1 transgenic rice plants matured earlier than the controls for about 19 days except DP0998.15 rice plants.

TABLE 18

Flowering trait, plant height and grain yield analysis of OsUSP1 transgenic rice plants at T₁ generation in Beijing

| Line ID | Days to heading date(d) | Diff of heading date | Days to maturity date (d) | Plant height (cm) | Effective panicle number per plant | Average grain yield per plant (g) |
|---------|------------------------|---------------------|---------------------------|-------------------|------------------------------------|-----------------------------------|
| ZH11-WT | 101 | 0 | 149 | 132.48 | 11.60 | 46.80 |
| ZH11-TC | 101 | / | 149 | 132.64 | 9.32 | 41.05 |
| DP0158 | 101 | 0 | 149 | 130.32 | 11.40 | 40.78 |
| DP0998.01 | 84 | 17 | 130 | 132.22 | 11.39 | 37.73 |
| DP0998.02 | 84 | 17 | 130 | 131.72 | 10.05 | 39.74 |
| DP0998.03 | 84 | 17 | 130 | 130.56 | 10.72 | 34.60 |
| DP0998.04 | 84 | 17 | 130 | 135.72 | 12.72 | 41.57 |
| DP0998.05 | 84 | 17 | 130 | 129.56 | 11.79 | 34.38 |
| DP0998.06 | 84 | 17 | 130 | 130.56 | 12.05 | 37.05 |
| DP0998.07 | 84 | 17 | 130 | 134.22 | 11.92 | 38.37 |
| DP0998.08 | 84 | 17 | 130 | 128.56 | 12.19 | 39.26 |
| DP0998.09 | 84 | 17 | 130 | 128.73 | 14.32 | 46.02 |
| DP0998.10 | 84 | 17 | 130 | 124.74 | 11.52 | 39.90 |
| DP0998.11 | 84 | 17 | 130 | 132.06 | 11.79 | 39.69 |
| DP0998.12 | 84 | 17 | 130 | 132.56 | 12.32 | 36.02 |
| DP0998.13 | 84 | 17 | 130 | 132.72 | 13.12 | 42.77 |
| DP0998.14 | 84 | 17 | 130 | 128.40 | 10.59 | 34.69 |
| DP0998.15 | 96 | 5 | 144 | 137.88 | 15.92 | 55.31 |

The plant height, effective panicle number and grain yield were measured. Table 19, 20 and 21 shows that the average grain yield per plant of OsUSP1 transgenic rice plants were lower than that of ZH11-WT, ZH11-TC and DP0158 controls, and the differences were not reach significant level; the effective panicle number of OsUSP1 transgenic rice plants were greater than ZH11-WT, ZH11-TC and DP0158 control plants; and there was no significant difference for the plant height for the transgenic and control plants.

TABLE 19

Grain yield analysis of OsUSP1 transgenic rice plants at T₁ generation at construct level

| Line ID | Yield per plant (g) | CK = ZH11-WT Diff | P value | P ≤ 0.1 | CK = ZH11-TC Diff | P value | P ≤ 0.1 | CK = DP0158 Diff | P value | P ≤ 0.1 |
|---------|---------------------|-------------------|---------|---------|-------------------|---------|---------|------------------|---------|---------|
| ZH11-WT | 46.80 | | | | | | | | | |
| ZH11-TC | 41.05 | | | | | | | | | |
| DP0158 | 40.78 | | | | | | | | | |
| DP0998 | 39.81 | −7.00 | 0.346 | | −1.25 | 0.866 | | −0.97 | 0.896 | |

TABLE 20

Plant height analysis of OsUSP1 transgenic rice plants at T₁ generation at construct level

| Line ID | Plant Height (cm) | CK = ZH11-WT Diff | P value | P ≤ 0.1 | CK = ZH11-TC Diff | P value | P ≤ 0.1 | CK = DP0158 Diff | P value | P ≤ 0.1 |
|---------|-------------------|-------------------|---------|---------|-------------------|---------|---------|------------------|---------|---------|
| ZH11-WT | 132.48 | | | | | | | | | |
| ZH11-TC | 132.64 | | | | | | | | | |
| DP0158 | 130.32 | | | | | | | | | |
| DP0998 | 131.35 | −1.13 | 0.357 | | −1.29 | 0.293 | | 1.03 | 0.404 | |

TABLE 21

Effective panicle number analysis of OsUSP1 transgenic
rice plants at $T_1$ generation at construct level

| Line ID | Panicle number | CK = ZH11-WT | | | CK = ZH11-TC | | | CK = DP0158 | | |
|---|---|---|---|---|---|---|---|---|---|---|
| | | Diff | P value | P ≤ 0.1 | Diff | P value | P ≤ 0.1 | Diff | P value | P ≤ 0.1 |
| ZH11-WT | 11.60 | | | | | | | | | |
| ZH11-TC | 9.32 | | | | | | | | | |
| DP0158 | 11.40 | | | | | | | | | |
| DP0998 | 12.16 | 0.56 | 0.488 | | 2.84 | 0.000 | Y | 0.76 | 0.346 | |

When obtained the $T_2$ seeds, we measured the fluorescent ratio of $T_2$ seeds under green fluorescent lamps. Analysis of the obtained $T_2$ seeds showed a 3:1 segregation ratio of fluorescent and non-fluorescent seeds, indicating that these transgenic individual plants contained a single copy of OsUSP1 gene.

Example 7

Flowering Trait Validation of OsUSP1 Transgenic Rice Plant

Optimal production requires the precise regulation of heading date or flowering time, which varies depending on planting location and climate.

To further investigate the flowering trait of OsUSP1 transgenic rice plants, $T_1$ and $T_2$ seeds were planted in different locations or environments: HN (Hainan, 18° 30'N, 109° 3'E), BJ (Beijing, 40° 13'N, 116° 13'E) and NX (Ningxia, 38° 36'N, 106° 23'E, altitude 1106.3 m).

The method is same to that described in Example 3.
Results:
$T_1$ Generation Plants
1) 2015 HN Five $T_1$ OsUSP1 transgenic plants were planted and the ZH11-TC was used as control. The days from sowing to heading date was 84 days for the ZH11-TC control, three lines exhibited the same heading date as the ZH11-TC control, one line showed two days earlier heading date, and one line showed two days later heading date. The maturity dates of these transgenic rice plants were similar to that of ZH11-TC plants. As shown in Table 22, the average grain yield of per plant of all the transgenic rice lines were less than that of ZH11-TC control.

TABLE 22

Flowering trait and grain yield analysis of OsUSP1 transgenic rice plants at $T_1$ generation in Hainan

| Line ID | Days to heading date (d) | Diff of heading date | Days to maturity date (d) | Average grain yield per plant (g) |
|---|---|---|---|---|
| ZH11-TC | 84 | / | 126 | 10.86 |
| DP0998.01 | 84 | 0 | 126 | 7.71 |
| DP0998.02 | 82 | 2 | 126 | 7.91 |
| DP0998.03 | 84 | 0 | 126 | 8.50 |
| DP0998.04 | 84 | 0 | 126 | 7.52 |
| DP0998.15 | 86 | 2 | 126 | 10.26 |

2) 2015 BJ

Six OsUSP1 transgenic rice lines were planted in Beijing paddy field, and ZH11-TC, DP0158 and DP0998.BN ($T_2$ non-fluorescent seeds segregated from the $T_2$ DP0998 transgenic seeds) were used as controls. The $T_1$ transgenic seeds and the control seeds were sowed on April 22, which was earlier than the sowing date in Beijing in previous year. At heading stage, the six OsUSP1 transgenic lines showed earlier heading date than the control plants (Table 23). These results confirmed the earlier heading trait of the OsUSP1 transgenic rice plants and demonstrated that the transgenic rice plants showed 7~14 days earlier heading date than the controls.

The OsUSP1 transgenic rice plants also matured earlier than the controls. The analysis of plant height, effective panicle number and grain yield indicates that OsUSP1 transgenic rice plants were shorter than all the control plants, and exhibited less panicle number and average grain yield per plant.

TABLE 23

Flowering trait, plant height and grain yield analysis of OsUSP1 transgenic rice plant at $T_1$ generation in Beijing ($2^{nd}$ experiment)

| Line ID | Days to heading date (d) | Diff of heading date | Days to maturity date (d) | Plant height (cm) | Effective panicle number per plant | Average grain yield per plant (g) |
|---|---|---|---|---|---|---|
| ZH11-TC | 105 | / | 150 | 129.25 | 12.50 | 43.05 |
| DP0158 | 105 | 0 | 150 | 133.17 | 11.42 | 30.29 |
| DP0998.BN | 105 | 0 | 150 | 123.75 | 13.50 | 29.30 |
| DP0998.02 | 93 | 12 | 139 | 118.34 | 10.33 | 32.54 |
| DP0998.04 | 93 | 12 | 139 | 121.13 | 13.00 | 38.32 |
| DP0998.08 | 92 | 13 | 139 | 113.70 | 9.96 | 33.80 |
| DP0998.10 | 93 | 12 | 139 | 107.99 | 9.48 | 31.78 |
| DP0998.12 | 91 | 14 | 137 | 114.36 | 9.23 | 30.25 |
| DP0998.15 | 98 | 7 | 144 | 122.98 | 9.84 | 36.27 |

3) 2015 NX

The same six OsUSP1 transgenic rice lines planted in Beijing were test in Ningxia, and ZH11-TC and DP0158 seedling were used as controls. Five OsUSP1 transgenic rice lines showed earlier heading date for about 17~19 days than ZH11-TC and DP0158 controls, and DP0998.15 rice plants headed earlier for eight days than the controls. These plants matured earlier for about 19 days than the controls. The plant height, effective panicle number, and the grain yield per plant were measured. The OsUSP1 transgenic rice plants were taller than both the controls, and exhibited more effective panicle number. The average grain yield per plant of OsUSP1 transgenic rice plants were greater than that of ZH11-TC and DP0158 plants because of cold temperature and later heading of the ZH11-TC and DP0158 plants.

TABLE 24

Flowering trait, plant height and grain yield analysis of OsUSP1 transgenic rice plants at $T_1$ generation in Ningxia

| Line ID | Days to heading date (d) | Diff of heading date | Days to maturity date (d) | Plant height (cm) | Effective panicle number per plant | Average grain yield per plant (g) |
|---|---|---|---|---|---|---|
| CY1-TC | 123 | 5 | 171 | 91.17 | 15.58 | 18.26 |
| ZH11-TC | 128 | / | 174 | 89.00 | 15.13 | 10.56 |
| DP0158 | 128 | 0 | 174 | 88.33 | 12.17 | 4.99 |
| DP0998.02 | 109 | 19 | 155 | 98.80 | 16.10 | 26.93 |
| DP0998.04 | 109 | 19 | 155 | 101.66 | 17.13 | 33.38 |
| DP0998.08 | 109 | 19 | 155 | 99.54 | 15.08 | 22.77 |
| DP0998.10 | 110 | 18 | 157 | 97.95 | 16.92 | 33.23 |
| DP0998.12 | 111 | 17 | 157 | 96.89 | 15.69 | 20.65 |
| DP0998.15 | 120 | 8 | 171 | 95.83 | 15.42 | 11.48 |

$T_2$ Generation Plant 1) 2015 HN $T_2$ seeds from six different plants of five OsUSP1 transgenic lines were planted in Hainan, and ZH11-TC rice plants were used as control. DP0998.02 rice plants showed three days earlier heading date than ZH11-TC plants and other transgenic plants have similar heading date as the ZH11-TC plants. These OsUSP1 transgenic rice and ZH11-TC plants matured at same time. The grain yield per plant of the OsUSP1 transgenic lines were less than that of ZH11-TC except DP0998.02.09 and DP0998.03.02 rice plants.

TABLE 25

Flowering trait, plant height and grain yield analysis of OsUSP1 transgenic rice plant at $T_2$ generation in Hainan

| Line ID | Days to heading date (d) | Diff of heading date | Days to maturity date (d) | Average grain yield per plant (g) |
|---|---|---|---|---|
| ZH11-TC | 84 | / | 126 | 9.78 |
| DP0998.01.02 | 84 | 0 | 126 | 7.83 |
| DP0998.02.01 | 81 | 3 | 126 | 7.62 |
| DP0998.02.09 | 81 | 3 | 126 | 9.66 |
| DP0998.03.02 | 83 | 0 | 126 | 11.42 |
| DP0998.04.01 | 83 | 0 | 126 | 6.01 |
| DP0998.15.01 | 83 | 0 | 126 | 6.15 |

2) 2015 Beijing $T_2$ OsUSP1 transgenic seeds were planted in Beijing field for two times. The sowing date of the first experiment is earlier than that in the previous year and the sowing date of the second experiment is similar to that in the previous year. The same OsUSP1 transgenic lines were planted and ZH11-TC, DP0158 and DP0998.BN rice plants were used as control and planted near the transgenic rice plants.

The twelve OsUSP1 transgenic rice lines showed 6~14 days earlier heading date than the controls in the first experiment and showed 3~11 days earlier heading date than controls except DP0998.15.61 and DP0998.15.62. The OsUSP1 transgenic rice plants also matured earlier than these controls. These results further demonstrate that $T_1$ and $T_2$ transgenic rice plants showed earlier heading trait in Beijing field.

Further analysis showed that the OsUSP1 transgenic rice plants were significantly shorter, and exhibited significantly less effective panicle number than ZH11-TC and DP0158 plants. The grain yield per plant of the OsUSP1 transgenic rice plants were less than that of ZH11-TC rice plants, and were similar to that of DP0158 and DP0998.BN rice plants in two experiments.

TABLE 26

Flowering trait, plant height and grain yield analysis of OsUSP1 transgenic rice plant at $T_2$ generation in Beijing ($1^{st}$ experiment)

| Line ID | Days to heading date (d) | Diff of heading date | Days to maturity date (d) | Plant height (cm) | Effective panicle number per plant | Average grain yield per plant (g) |
|---|---|---|---|---|---|---|
| ZH11-TC | 105 | / | 150 | 129.25 | 12.50 | 43.05 |
| DP0158 | 105 | 0 | 150 | 133.17 | 11.42 | 30.29 |
| DP0998.BN | 105 | 0 | 150 | 123.75 | 13.50 | 29.30 |
| DP0998.02.69 | 91 | 14 | 138 | 120.05 | 10.07 | 26.52 |
| DP0998.03.62 | 91 | 14 | 138 | 119.25 | 10.19 | 31.90 |
| DP0998.04.61 | 91 | 14 | 138 | 113.66 | 10.19 | 27.87 |
| DP0998.04.62 | 91 | 14 | 138 | 113.18 | 9.55 | 24.98 |
| DP0998.08.66 | 91 | 14 | 138 | 102.73 | 9.47 | 22.36 |
| DP0998.08.67 | 91 | 14 | 138 | 109.62 | 9.91 | 25.42 |
| DP0998.10.61 | 92 | 13 | 138 | 109.29 | 9.69 | 27.76 |
| DP0998.10.62 | 92 | 13 | 138 | 117.74 | 9.91 | 35.15 |
| DP0998.12.61 | 95 | 10 | 141 | 121.33 | 9.81 | 29.57 |
| DP0998.12.62 | 95 | 10 | 141 | 124.93 | 10.43 | 40.54 |
| DP0998.15.61 | 99 | 6 | 145 | 127.23 | 10.59 | 39.25 |
| DP0998.15.62 | 99 | 6 | 145 | 126.43 | 10.46 | 42.05 |

TABLE 27

Flowering trait, plant height and grain yield analysis of OsUSP1 transgenic rice plant at $T_2$ generation in Beijing ($2^{nd}$ experiment)

| Line ID | Days to heading date (d) | Diff of heading date | Days to maturity date (d) | Plant height (cm) | Effective panicle number per plant | Average grain yield per plant (g) |
|---|---|---|---|---|---|---|
| ZH11-TC | 96 | / | 139 | 130.67 | 8.77 | 56.74 |
| DP0158 | 96 | 0 | 139 | 131.17 | 10.17 | |
| DP0998.BN | 96 | 0 | 139 | 136.67 | 11.50 | 32.24 |
| DP0998.02.69 | 85 | 11 | 130 | 121.67 | 9.71 | 26.90 |
| DP0998.03.62 | 91 | 5 | 135 | 121.83 | 9.52 | 32.79 |
| DP0998.04.61 | 87 | 9 | 131 | 124.04 | 9.20 | 34.28 |
| DP0998.04.62 | 87 | 9 | 131 | 126.09 | 8.88 | 31.59 |
| DP0998.08.66 | 87 | 9 | 131 | 114.88 | 8.69 | 27.67 |
| DP0998.08.67 | 87 | 9 | 131 | 115.67 | 9.33 | 31.27 |
| DP0998.10.61 | 87 | 9 | 131 | 113.14 | 9.52 | 31.37 |
| DP0998.10.62 | 91 | 5 | 135 | 116.93 | 10.03 | 39.39 |
| DP0998.12.61 | 91 | 5 | 135 | 119.61 | 8.75 | 29.95 |
| DP0998.12.62 | 93 | 3 | 135 | 125.77 | 9.65 | 37.39 |
| DP0998.15.61 | 96 | 0 | 139 | 127.04 | 9.78 | 34.35 |
| DP0998.15.62 | 96 | 0 | 139 | 133.51 | 10.10 | 37.89 |

3) 2015 NX

Twelve $T_2$ seeds from seven OsUSP1 transgenic lines were planted in the Ningxia, and ZH11-TC and DP0158 plants were used as controls. The ZH11-TC and DP0158 plants were shown heading panicle at 128 d after seeding, and the transgenic rice plants showed 12~22 days earlier heading date than the control plants except DP0998.15.61 and DP0998.15.62. The ZH11-TC and DP0158 plant matured at 175 d after seeding, while the OsUSP1 transgenic rice plants matured earlier and avoided the low temperature in the later maturity stage.

The plant height and the grain yield were measured. As shown in Table 28. All the OsUSP1 transgenic rice plants were taller and had greater grain yield than the ZH11-TC and DP0158 plants.

TABLE 28

Flowering trait, plant height and grain yield analysis of OsUSP1 transgenic rice plants at T$_2$ generation in Ningxia

| Line ID | Days to heading date (d) | Diff of heading date | Days to maturity date (d) | Plant height (cm) | Effective panicle number per plant | Average grain yield per plant (g) |
|---|---|---|---|---|---|---|
| ZH11-TC | 128 | / | 175 | 89.00 | 15.13 | 10.56 |
| DP0158 | 128 | 0 | 175 | 88.33 | 12.17 | 4.99 |
| DP0998.02.69 | 110 | 18 | 155 | 89.70 | 10.07 | 20.66 |
| DP0998.03.62 | 109 | 19 | 155 | 93.69 | 10.89 | 22.50 |
| DP0998.04.61 | 108 | 20 | 153 | 94.36 | 12.39 | 22.71 |
| DP0998.04.62 | 109 | 19 | 155 | 97.02 | 13.67 | 24.40 |
| DP0998.08.66 | 109 | 19 | 155 | 93.80 | 10.65 | 22.52 |
| DP0998.08.67 | 106 | 22 | 151 | 94.80 | 10.42 | 21.53 |
| DP0998.10.61 | 110 | 18 | 155 | 93.80 | 13.78 | 30.29 |
| DP0998.10.62 | 113 | 15 | 162 | 96.46 | 13.44 | 28.06 |
| DP0998.12.61 | 115 | 13 | 167 | 96.58 | 13.55 | 22.39 |
| DP0998.12.62 | 116 | 12 | 167 | 94.36 | 12.04 | 12.68 |
| DP0998.15.61 | 117 | 11 | 167 | 95.02 | 15.29 | 11.29 |
| DP0998.15.62 | 120 | 8 | 171 | 97.24 | 14.13 | 8.33 |

Example 8

Field Drought Test for OsUSP1 Transgenic Rice Plants

Figure 4:
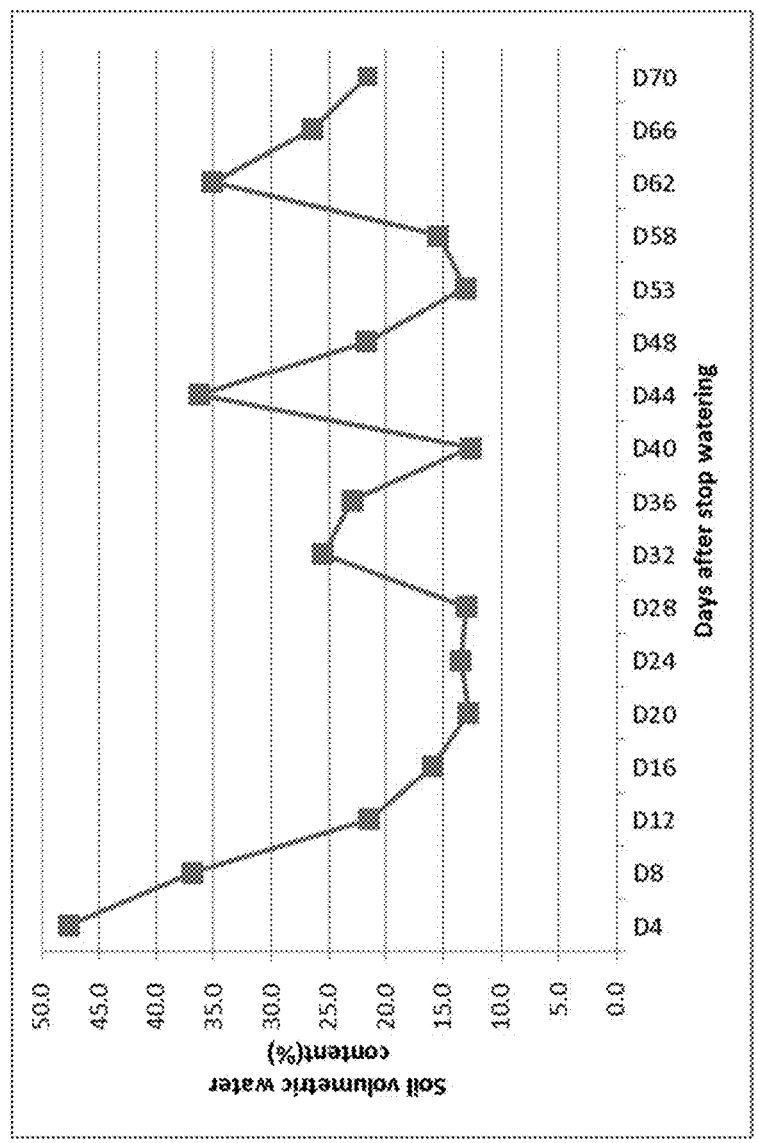
FIG. 4 shows changes of soil volumetric moisture content at different developmental stage in Ningxia field experiment for drought testing OsUSP1 transgenic rice. The OsUSP1 transgenic rice started heading at 22 days after stopping watering and ZH11-TC rice plants started heading at 43 d after stopping watering.

The OsUSP1 transgenic rice plants were drought test in Ningxia, the results as below:

Field Drought Assay Results:

Twelve OsUSP1 transgenic lines were tested in Ningxia Province. ZH11-TC, DP0158 and DP0998.BN planted nearby were used as controls. Watering was stopped from panicle initiation stage II ZH11-TC rice plants to seed maturity to produce heavier drought stress. The soil volumetric water content decreased from 48% to 12% before heading stage of OsUSP1 transgenic rice plants, two rainfalls increased the water content of the field after the heading stage of OsUSP1 transgenic rice and ZH11-TC rice plants (FIG. 4). The OsUSP1 transgenic rice plants headed earlier for about 18~25 days than the controls except DP0998.15.61 transgenic lines and DP0995.15.61 headed later than these controls for about three days. At the end, the OsUSP1 transgenic rice plants matured earlier than these controls, which were not fully mature because of cold temperature in the later stage. The OsUSP1 transgenic rice plants suffered shorter time drought stress than the ZH11-TC and DP0158 control plants. As shown in Table 29, all the lines obtained greater grain yields per plant than the control plants. These results demonstrate that OsUSP1 rice plant had greater grain yield per plant than control after drought stress.

TABLE 29

Grain yield analysis of OsUSP1 transgenic rice plants under field drought conditions

| Line ID | Number of survival plants | Number of harvested plants | Diff of heading date | Yield per plant (g) | CK = ZH11-TC Diff | P value | P ≤ 0.1 | CK = DP0158 Diff | P value | P ≤ 0.1 | CK = DP0998.BN Diff | P value | P ≤ 0.1 |
|---|---|---|---|---|---|---|---|---|---|---|---|---|---|
| DP0998 (Construct) | | | | 6.36 | 3.46 | 0.005 | Y | 6.44 | 0.000 | Y | 4.83 | 0.000 | Y |
| ZH11-TC | 38 | 17 | / | 2.91 | | | | | | | | | |
| DP0158 | 39 | 8 | 0 | 0.08 | | | | | | | | | |
| DP0998.BN | 38 | 20 | 0 | 1.53 | | | | | | | | | |
| DP0998.01.61 | 38 | 22 | 25 | 7.29 | 4.38 | 0.001 | Y | 7.36 | 0.000 | Y | 5.76 | 0.000 | Y |
| DP0998.02.69 | 39 | 26 | 25 | 8.13 | 5.22 | 0.000 | Y | 8.20 | 0.000 | Y | 6.60 | 0.000 | Y |
| DP0998.03.61 | 39 | 23 | 18 | 8.15 | 5.24 | 0.000 | Y | 8.22 | 0.000 | Y | 6.62 | 0.000 | Y |
| DP0998.05.67 | 37 | 18 | 25 | 7.81 | 4.91 | 0.000 | Y | 7.89 | 0.000 | Y | 6.28 | 0.000 | Y |
| DP0998.06.70 | 33 | 17 | 15 | 6.34 | 3.43 | 0.014 | Y | 6.41 | 0.000 | Y | 4.81 | 0.000 | Y |
| DP0998.07.61 | 40 | 24 | 18 | 4.87 | 1.97 | 0.147 | | 4.95 | 0.000 | Y | 3.34 | 0.002 | Y |
| DP0998.08.61 | 40 | 24 | 25 | 5.86 | 2.96 | 0.033 | Y | 5.94 | 0.000 | Y | 4.33 | 0.000 | Y |
| DP0998.09.61 | 40 | 24 | 18 | 4.43 | 1.53 | 0.270 | | 4.51 | 0.000 | Y | 2.90 | 0.006 | Y |
| DP0998.10.64 | 40 | 24 | 15 | 4.68 | 1.78 | 0.199 | | 4.76 | 0.000 | Y | 3.15 | 0.004 | Y |
| DP0998.13.61 | 39 | 26 | 18 | 7.42 | 4.51 | 0.001 | Y | 7.49 | 0.000 | Y | 5.89 | 0.000 | Y |
| DP0998.14.61 | 26 | 15 | 25 | 7.68 | 4.77 | 0.001 | Y | 7.75 | 0.000 | Y | 6.15 | 0.000 | Y |
| DP0998.15.61 | 39 | 24 | 3 | 3.69 | 0.79 | 0.560 | | 3.77 | 0.003 | Y | 2.16 | 0.050 | Y |

Example 9

Laboratory Paraquat Assays of OsMBD1 Transgenic Rice Plants

Paraquat (1,1-dimethyl-4,4-bipyridinium dichloride), is a foliar-applied and non-selective bipyridinium herbicide, and it is one of the most widely used herbicides in the world, controlling weeds in a huge variety of crops like corn, rice, soybean etc. In plant cells, paraquat mainly targets chloroplasts by accepting electrons from photosystem I and then reacting with oxygen to produce superoxide and hydrogen peroxide, which cause photooxidative stress. Drought stress usually leads to increased reactive oxygen species (ROS) in plants and sometimes, the drought tolerance of plant is associated with enhanced antioxidative ability. Paraquat is a potent oxidative stress inducer; it greatly increases the ROS production and inhibits the regeneration of reducing equivalents and compounds necessary for the activity of the antioxidant system. The ROS generation is enhanced under abiotic stress conditions, and the plant responses range from tolerance to death depending on the stress intensity and its associated-ROS levels. Relative low level of paraquat can mimic the stress-associated ROS production and used as a stress tolerance marker in plant stress biology (Hasaneen M. N. A. (2012) Herbicide-Properties, Synthesis and Control of Weeds book). Therefore, the paraquat tolerance of the drought tolerant transgenic rice plants was tested.

Paraquat Assay Methods:

Transgenic rice plants from ten transgenic lines were tested by paraquat assay. Tissue-cultured Zhonghua 11 plants (ZH11-TC) and empty vector transgenic plants (DP0158) were used as controls. $T_2$ transgenic seeds were sterilized and germinated as described in Example 3, and this assay was carried out in growth room with temperature at 28~30° C. and humidity ~30%. The germinated seeds were placed in a tube with a hole at the bottom, and water cultured at 30° C. for 5 days till one-leaf and one-terminal bud stage. Uniform seedlings about 3.5~4 cm in height were selected for paraquat testing. Randomized block design was used in this experiment. There were five blocks, each of which has 16×12 holes. Each transgenic line was placed in one row (12 plants/line), and ZH11-TC and DP0158 seedlings were placed in 3 rows (3×12 plants) randomly in one block. Then the seedlings were treated with 0.8 μM paraquat solution for 7 days at 10 h day/14 h night, and the treated seedlings first encountered dark and took up the paraquat solution which was changed every two days. After treated for 7 days, the green seedlings were counted. Those seedlings that maintain green in whole without damage were considered as paraquat tolerant seedling; those with bleached leaves or stem were not considered as paraquat tolerant seedling.

Tolerance rate was used as a parameter for this trait screen, which is the percentage of plants which kept green and showed tolerant phenotype over the total plant number.

The data was analyzed at construct level (all transgenic plants compared with the control) and transgenic line level (different transgenic lines compared with the control) using a statistic model of "Y~seg+line (seg)+rep+error", random effect of "rep", Statistic Method of "SAS® PROC GLIMMIX".

Paraquat Assay Results:

In the first experiment, 459 of the 600 transgenic seedlings (71%) kept green and showed tolerant phenotype after treated with 0.8 μM paraquat solutions for 7 days, while 105 of the 180 (58%) seedlings from ZH11-TC showed tolerant phenotype and 118 of the 180 (66%) seedlings from DP0158 showed tolerant phenotype. The tolerance rate of OsMBD1 transgenic seedlings was significantly higher than that of ZH11-TC and DP0158 controls. Analysis at transgenic line level is displayed in Table 30. Four OsMBD1 transgenic lines had significantly higher tolerance rates than either ZH11-TC or DP0158 controls, and the tolerance rates of four lines were more than 80%. These results show that overexpression OsMBD1 gene increased the paraquat tolerance or antioxidative ability of the transgenic plants.

TABLE 30

Paraquat tolerance assay of OsMBD1 transgenic rice plants (1$^{st}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0995 (Construct) | 459 | 600 | 77 | 0.0000 | Y | 0.0030 | Y |
| ZH11-TC | 105 | 180 | 58 | | | | |
| DP0158 | 118 | 180 | 66 | | | | |
| DP0995.01 | 42 | 60 | 70 | 0.1150 | | 0.5297 | |
| DP0995.02 | 52 | 60 | 87 | 0.0004 | Y | 0.0040 | Y |
| DP0995.05 | 48 | 60 | 80 | 0.0045 | Y | 0.0425 | Y |
| DP0995.09 | 42 | 60 | 70 | 0.1150 | | 0.5297 | |
| DP0995.10 | 42 | 60 | 70 | 0.1150 | | 0.5297 | |
| DP0995.12 | 43 | 60 | 72 | 0.0725 | | 0.3871 | |
| DP0995.13 | 47 | 60 | 78 | 0.0082 | Y | 0.0718 | |
| DP0995.14 | 51 | 60 | 85 | 0.0007 | Y | 0.0074 | Y |
| DP0995.15 | 49 | 60 | 82 | 0.0024 | Y | 0.0243 | Y |
| DP0995.16 | 43 | 60 | 72 | 0.0725 | | 0.3871 | |

In the second experiment, 517 of the 600 OsMBD1 transgenic seedlings (86%) kept green and showed tolerant phenotype after treated with paraquat solution, whereas only 108 of the 180 (60%) ZH11-TC seedlings, and 115 of the 180 (64%) DP0158 seedlings showed tolerant phenotype. The tolerance rate of OsMBD1 transgenic plants was significantly higher than that of the ZH11-TC and DP0158 control at the construct level. The analysis at transgenic line level is displayed in Table 31. Eight lines had significant greater tolerance rates than either ZH11-TC or DP0158 seedlings, which further demonstrates that OsMBD1 transgenic rice plants had enhanced paraquat tolerance at construct and transgenic line level at seedling stages. Overexpression of OsMBD1 gene improved the paraquat tolerance of the transgenic plants.

TABLE 31

Paraquat tolerance assay of OsMBD1 transgenic rice plants (2$^{nd}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0995 (Construct) | 517 | 600 | 86 | 0.0000 | Y | 0.0000 | Y |
| ZH11-TC | 108 | 180 | 60 | | | | |
| DP0158 | 115 | 180 | 64 | | | | |
| DP0995.01 | 47 | 60 | 78 | 0.0136 | Y | 0.0441 | Y |
| DP0995.02 | 44 | 60 | 73 | 0.0688 | | 0.1846 | |
| DP0995.05 | 46 | 60 | 77 | 0.0241 | Y | 0.0739 | |
| DP0995.09 | 48 | 60 | 80 | 0.0075 | Y | 0.0254 | Y |
| DP0995.10 | 54 | 60 | 90 | 0.0002 | Y | 0.0007 | Y |
| DP0995.12 | 57 | 60 | 95 | 0.0000 | Y | 0.0002 | Y |
| DP0995.13 | 57 | 60 | 95 | 0.0000 | Y | 0.0002 | Y |
| DP0995.14 | 58 | 60 | 97 | 0.0001 | Y | 0.0003 | Y |
| DP0995.15 | 51 | 60 | 85 | 0.0011 | Y | 0.0041 | Y |
| DP0995.16 | 55 | 60 | 92 | 0.0001 | Y | 0.0004 | Y |

Example 10

Laboratory Paraquat Assays of OsUSP1 Transgenic Rice Plants

OsUSP1 transgenic rice plants were tested using the paraquat assay method descried in Example 9. The paraquat assay results is shown below:

In the first experiment, 540 of the 600 transgenic seedlings (90%) kept green and showed tolerant phenotype after treated with 0.8 μM paraquat solutions for 7 days, while 132 of the 180 (73%) seedlings from ZH11-TC showed tolerant phenotype and 118 of the 180 (66%) seedlings from DP0158 showed tolerant phenotype. The tolerance rate of OsUSP1 transgenic seedlings was significantly higher than that of ZH11-TC and DP0158 controls. Analysis at transgenic line level is displayed in Table 32. Seven OsUSP1 transgenic lines had significantly higher tolerance rates than either ZH11-TC or DP0158 controls, and the tolerance rates of all transgenic lines were more than 80%. These results show that over-expression OsUSP1 gene increased the paraquat tolerance or antioxidative ability of the transgenic plants.

TABLE 32

Paraquat tolerance assay of OsUSP1 transgenic rice plants (1$^{st}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0998 (Construct) | 540 | 600 | 90 | 0.0000 | Y | 0.0000 | Y |
| ZH11-TC | 132 | 180 | 73 | | | | |
| DP0158 | 118 | 180 | 66 | | | | |
| DP0998.01 | 53 | 60 | 88 | 0.0234 | Y | 0.0024 | Y |
| DP0998.02 | 52 | 60 | 87 | 0.0425 | Y | 0.0044 | Y |
| DP0998.03 | 57 | 60 | 95 | 0.0026 | Y | 0.0004 | Y |
| DP0998.05 | 49 | 60 | 82 | 0.2015 | | 0.0263 | Y |
| DP0998.06 | 60 | 60 | 100 | 0.0000 | Y | 0.0000 | Y |
| DP0998.07 | 56 | 60 | 93 | 0.0040 | Y | 0.0005 | Y |
| DP0998.08 | 50 | 60 | 83 | 0.1256 | | 0.0147 | Y |
| DP0998.10 | 56 | 60 | 93 | 0.0040 | Y | 0.0005 | Y |
| DP0998.13 | 48 | 60 | 80 | 0.3072 | | 0.0455 | Y |
| DP0998.14 | 59 | 60 | 98 | 0.0039 | Y | 0.0013 | Y |

In the second experiment, 521 of the 600 OsUSP1 transgenic seedlings (87%) kept green and showed tolerant phenotype after treated with paraquat solution, whereas 123 of the 180 (68%) ZH11-TC seedlings, and 127 of the 180 (71%) DP0158 seedlings showed tolerant phenotype. The tolerance rate of OsUSP1 transgenic plants was significantly higher than that of the ZH11-TC and DP0158 control at the construct level. The analysis at transgenic line level is displayed in Table 33. Sevens lines had significant greater tolerance rates than either ZH11-TC or DP0158 seedlings, which further demonstrates that OsUSP1 transgenic rice plants had enhanced paraquat tolerance at construct and transgenic line level at seedling stages. Over-expression of OsUSP1 gene improved the paraquat tolerance of the transgenic plants.

TABLE 33

Paraquat tolerance assay of OsUSP1 transgenic rice plants ($2^{nd}$ experiment)

| Line ID | Number of tolerant seedlings | Number of total seedlings | Tolerant rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0998 (Construct) | 521 | 600 | 87 | 0.0000 | Y | 0.0000 | Y |
| ZH11-TC | 123 | 180 | 68 | | | | |
| DP0158 | 127 | 180 | 71 | | | | |
| DP0998.01 | 57 | 60 | 95 | 0.0007 | Y | 0.0013 | Y |
| DP0998.02 | 53 | 60 | 88 | 0.0051 | Y | 0.0101 | Y |
| DP0998.03 | 58 | 60 | 97 | 0.0008 | Y | 0.0012 | Y |
| DP0998.05 | 51 | 60 | 85 | 0.0546 | | 0.1001 | |
| DP0998.06 | 51 | 60 | 85 | 0.0174 | Y | 0.0338 | Y |
| DP0998.07 | 55 | 60 | 92 | 0.0016 | Y | 0.0031 | Y |
| DP0998.08 | 45 | 60 | 75 | 0.3340 | | 0.5111 | |
| DP0998.10 | 52 | 60 | 87 | 0.0095 | Y | 0.0187 | Y |
| DP0998.13 | 56 | 60 | 93 | 0.0010 | Y | 0.0018 | Y |
| DP0998.14 | 43 | 60 | 72 | 0.6301 | | 0.8703 | |

What is claimed is:

1. A method of producing a plant having an early flowering time, the method comprising:
   (a) introducing in a plant cell a recombinant DNA construct comprising a polynucleotide encoding a polypeptide comprising an amino acid sequence of at least 95% sequence identity compared to SEQ ID NO: 4; and
   (b) generating the plant, wherein the plant comprises in its genome the recombinant DNA construct and has an early flowering time as compared to a control plant not comprising the recombinant DNA construct.

2. The method of claim 1, wherein the polynucleotide is operably linked to at least one heterologous regulatory element.

3. The method of claim 2, wherein the plant has an earlier flowering time by about 5~23 days when compared to the control plant.

4. The method of claim 1, wherein the plant is selected from the group consisting of rice, maize, soybean, sunflower, sorghum, canola, wheat, alfalfa, cotton, barley, millet, sugar cane and switchgrass.

5. The method of claim 2, wherein the heterologous regulatory element is a heterologous promoter.

* * * * *

SEQUENCE LISTING

<160> NUMBER OF SEQ ID NOS: 15

<210> SEQ ID NO 1
<211> LENGTH: 11934
<212> TYPE: DNA
<213> ORGANISM: Artificial Sequence
<220> FEATURE:
<223> OTHER INFORMATION: The nucleotide sequence of vector DP0158

<400> SEQUENCE: 1

```
gaattctcta gtcccgatct agtaacatag atgacaccgc gcgcgataat ttatcctagt      60
ttgcgcgcta tattttgttt tctatcgcgt attaaatgta taattgcggg actctaatca     120 taaaaccca tctcataaat aacgtcatgc attacatgtt aattattaca tgcttaacgt      180
aattcaacag aaattatatg ataatcatcg caagaccggc aacaggattc aatcttaaga     240
aacgcggccg cttcagttgt ggcccagctt ggaggtcgac tcgcgaggat ctctgcagag     300
agatagattt gtagagagag actggtgatt tcagcgtgtc ctctccaaat gaaatgaact     360
tccttatata gaggaagggt cttgcgaagg atagtgggat tgtgcgtcat cccttacgtc     420
agtggagata tcacatcaat ccacttgctt tgaagacgtg gttggaacgt cttcttttc      480 cacgatgctc ctcgtgggtg ggggtccatc tttgggacca ctgtcggcag aggcatcttg     540
aacgatagcc tttcctttat cgcaatgatg gcatttgtag gtgccacctt cctttctac      600 tgtccttttg atgaagtgac agatagctgg gcaatggaat ccgaggaggt ttcccgatat     660
```

```
tacccttttgt tgaaaagtct caatagccct ttggtcttct gagactgtat ctttgatatt    720
cttggagtag acgagagtgt cgtgctccac catgttcaca tcaatccact tgctttgaag    780
acgtggttgg aacgtcttct ttttccacga tgctcctcgt gggtgggggt ccatctttgg    840
gaccactgtc ggcagaggca tcttgaacga tagccttttcc tttatcgcaa tgatggcatt    900
tgtaggtgcc accttccttt tctactgtcc ttttgatgaa gtgacagata gctgggcaat    960
ggaatccgag gaggtttccc gatattaccc tttgttgaaa agtctcaata gcccttggt    1020
cttctgagac tgtatctttg atattcttgg agtagacgag agtgtcgtgc tccaccatgt   1080
tgccaagctg ctctaagctt tggcggccgc attcgcaaaa cacacctaga ctagatttgt   1140
tttgctaacc caattgatat taattatata tgattaatat ttatatgtat atggatttgg   1200
ttaatgaaat gcatctggtt catcaaagaa ttataaagac acgtgacatt catttaggat   1260
aagaaatatg gatgatctct ttctctttta ttcagataac tagtaattac acataacaca   1320
caactttgat gcccacatta tagtgattag catgtcacta tgtgtgcatc cttttatttc   1380
atacattaat taagttggcc aatccagaag atggacaagt ctaggttaac catgtggtac   1440
ctacgcgttc gaatatccat gggccgctac aggaacaggt ggtggcggcc ctcggtgcgc   1500
tcgtactgct ccacgatggt gtagtcctcg ttgtgggagg tgatgtccag cttggcgtcc   1560
acgtagtagt agccgggcag ctgcacgggc ttcttggcca tgtagatgga cttgaactcc   1620
accaggtagt ggccgccgtc cttcagcttc agggccttgt gggtctcgcc cttcagcacg   1680
ccgtcgcggg ggtacaggcg ctcggtggag gcctcccagc ccatggtctt cttctgcatc   1740
acggggccgt cggaggggaa gttcacgccg atgaacttca ccttgtagat gaagcagccg   1800
tcctgcaggg aggagtcctg ggtcacggtc gccacgccgc cgtcctcgaa gttcatcacg   1860
cgctcccact gaagccctc ggggaaggac agcttcttgt agtcgggat gtcggcgggg   1920
tgcttcacgt acaccttgga gccgtactgg aactgggggg acaggatgtc ccaggcgaag   1980
ggcaggggc cgcccttcgt caccttcagc ttcacggtgt tgtggccctc gtaggggcgg   2040
ccctcgccct cgccctcgat ctcgaactcg tggccgttca cggtgccctc catgcgcacc   2100
ttgaagcgca tgaactcggt gatgacgttc tcggaggagg ccatggtggc gaggatctac   2160
tcggctacac tcacacgctc gctctcgcag ttgcaggtgt aagtttctag ctagggcact   2220
cacggggtac gtatttgtag ccagccacgc acggtctgag ctcgccatgt gccgccatgc   2280
atgcgggggc acgtcgccag cgtacgcggc catcgtcgct gacgaaggta gcgcattcaa   2340
gtccggtcgg tagaggtcag ctgggtcgtt cgccgatggt agttgccgcc cggactcagt   2400
gggcggtagg cgaaggctag caagcagacg actccattca tgcgcatcat ccaaaggtga   2460
tgcaaagcct tccaaacgcg attgtctcat gatgtttccg tctcttgtta cgaggagtac   2520
aattttttct tatacacgaa cgttacttta tgtcacattt ccatgccatg aacaccttgg   2580
cttcaaataa gtgagtgttt ttttcacat tctgtggcat aaacagaatt ctagagtgg   2640
catttgtgat acattgtgaa agctaagagt ggtaaaagta aaataaaatt gttttgcttt   2700
tgccgcggaa tggaaattat ttgtcaaaac ctaagagtgg caaaactgaa atgtcaaaac   2760
ctagagtgac ataaacaaaa tttacccatc actaaatgag cacaaaatat ttcaccacaa   2820
tggaggtatg tgaggtccga tgtactacta gagctcatcg gaaaagcatc ctcttgatga   2880
gtaaacctct tgaagtactg taccaccaca tttatttat cctcatcggc ttatttttag   2940
gccacggtta ttctcacgaa gagacggtta acccttctcg tagactacac atcgagatcc   3000
actagttcta gagcggccag cttcgaagct tggcactggc cgtcgtttta caacgtcgtg   3060
```

```
actgggaaaa ccctggcgtt acccaactta atcgccttgc agcacatccc cctttcgcca    3120
gctggcgtaa tagcgaagag gcccgcaccg atcgcccttc ccaacagttg cgcagcctga    3180
atggcgaatg ctagagcagc ttgagcttgg atcagattgt cgtttccgc cttcagttta     3240
aactatcagt gtttgacagg atatattggc gggtaaacct aagagaaaag agcgtttatt    3300
agaataatcg gatatttaaa agggcgtgaa aaggtttatc cgttcgtcca tttgtatgtg    3360
catgccaacc acagggttcc cctcgggatc aaagtacttt gatccaaccc ctccgctgct    3420
atagtgcagt cggcttctga cgttcagtgc agccgtcttc tgaaaacgac atgtcgcaca    3480
agtcctaagt tacgcgacag gctgccgccc tgcccttttc ctggcgtttt cttgtcgcgt    3540
gttttagtcg cataaagtag aatacttgcg actagaaccg gagacattac gccatgaaca    3600
agagcgccgc cgctggcctg ctgggctatg cccgcgtcag caccgacgac caggacttga    3660
ccaaccaacg ggccgaactg cacgcggccg gctgcaccaa gctgttttcc gagaagatca    3720
ccggcaccag gcgcgaccgc ccggagctgg ccaggatgct tgaccaccta cgccctggcg    3780
acgttgtgac agtgaccagg ctagaccgcc tggcccgcag cacccgcgac ctactggaca    3840
ttgccgagcg catccaggag gccggcgcgg gcctgcgtag cctggcagag ccgtgggccg    3900
acaccaccac gccggccggc cgcatggtgt tgaccgtgtt cgccggcatt gccgagttcg    3960
agcgttccct aatcatcgac cgcacccgga gcgggcgcga ggccgccaag gcccgaggcg    4020
tgaagtttgg ccccgccct accctcaccc cggcacagat cgcgcacgcc cgcgagctga    4080
tcgaccagga aggccgcacc gtgaaagagg cggctgcact gcttggcgtg catcgctcga    4140
ccctgtaccg cgcacttgag cgcagcgagg aagtgacgcc caccgaggcc aggcggcgcg    4200
gtgccttccg tgaggacgca ttgaccgagg ccgacgccct ggcggccgcc gagaatgaac    4260
gccaagagga caagcatga aaccgcacca ggacggccag gacgaaccgt ttttcattac    4320
cgaagagatc gaggcggaga tgatcgcggc cgggtacgtg ttcgagccgc ccgcgcacgt    4380
ctcaaccgtg cggctgcatg aaatcctggc cggtttgtct gatgccaagc tggcggcctg    4440
gccggccagc ttggccgctg aagaaaccga gcgccgccgt ctaaaaaggt gatgtgtatt    4500
tgagtaaaac agcttgcgtc atgcggtcgc tgcgtatatg atgcgatgag taaataaaca    4560
aatacgcaag gggaacgcat gaaggttatc gctgtactta accagaaagg cgggtcaggc    4620
aagacgacca tcgcaaccca tctagcccgc gccctgcaac tcgccggggc cgatgttctg    4680
ttagtcgatt ccgatcccca gggcagtgcc cgcgattggg cggccgtgcg gaagatcaa     4740
ccgctaaccg ttgtcggcat cgaccgcccg acgattgacc gcgacgtgaa ggccatcggc    4800
cggcgcgact tcgtagtgat cgacggagcg ccccaggcgg cggacttggc tgtgtccgcg    4860
atcaaggcag ccgacttcgt gctgattccg gtgcagccaa gccttacga catatgggcc    4920
accgccgacc tggtggagct ggttaagcag cgcattgagg tcacggatgg aaggctacaa    4980
gcggcctttg tcgtgtcgcg ggcgatcaaa ggcacgcgca tcggcggtga ggttgccgag    5040
gcgctggccg ggtacgagct gcccattctt gagtcccgta tcacgcagcg cgtgagctac    5100
ccaggcactg ccgccgccgg cacaaccgtt cttgaatcag aacccgaggg cgacgctgcc    5160
cgcgaggtcc aggcgctggc cgctgaaatt aaatcaaaac tcatttgagt taatgaggta    5220
aagagaaaat gagcaaaagc acaaacacgc taagtgccgg ccgtccgagc gcacgcagca    5280
gcaaggctga acgttggcc agcctggcag acacgccagc catgaagcgg gtcaactttc     5340
agttgccggc ggaggatcac accaagctga agatgtacgc ggtacgccaa ggcaagacca    5400
```

```
ttaccgagct gctatctgaa tacatcgcgc agctaccaga gtaaatgagc aaatgaataa      5460
atgagtagat gaattttagc ggctaaagga ggcggcatgg aaaatcaaga caaccaggc      5520
accgacgccg tggaatgccc catgtgtgga ggaacgggcg gttggccagg cgtaagcggc      5580
tgggttgtct gccggccctg caatggcact ggaaccccca agcccgagga atcggcgtga      5640
cggtcgcaaa ccatccggcc cggtacaaat cggcgcggcg ctgggtgatg acctggtgga      5700
gaagttgaag gccgcgcagg ccgcccagcg gcaacgcatc gaggcagaag cacgccccgg      5760
tgaatcgtgg caagcggccg ctgatcgaat ccgcaaagaa tcccggcaac cgccggcagc      5820
cggtgcgccg tcgattagga agccgcccaa gggcgacgag caaccagatt ttttcgttcc      5880
gatgctctat gacgtgggca cccgcgatag tcgcagcatc atggacgtgg ccgttttccg      5940
tctgtcgaag cgtgaccgac gagctggcga ggtgatccgc tacgagcttc agacgggca      6000
cgtagaggtt ccgcagggc cggccggcat ggccagtgtg tgggattacg acctggtact      6060
gatggcggtt tccatctaa ccgaatccat gaaccgatac cgggaaggga agggagacaa      6120
gcccggccgc gtgttccgtc cacacgttgc ggacgtactc aagttctgcc ggcgagccga      6180
tggcggaaag cagaaagacg acctggtaga aacctgcatt cggttaaaca ccacgcacgt      6240
tgccatgcag cgtacgaaga aggccaagaa cggccgcctg gtgacggtat ccagggtga      6300
agccttgatt agccgctaca agatcgtaaa gagcgaaacc gggcggccgg agtacatcga      6360
gatcgagcta gctgattgga tgtaccgcga gatcacagaa ggcaagaacc cggacgtgct      6420
gacggttcac cccgattact ttttgatcga tcccggcatc ggccgttttc tctaccgcct      6480
ggcacgccgc gccgcaggca aggcagaagc cagatggttg ttcaagacga tctacgaacg      6540
cagtggcagc gccggagagt tcaagaagtt ctgtttcacc gtgcgcaagc tgatcgggtc      6600
aaatgacctg ccggagtacg atttgaagga ggaggcgggg caggctggcc cgatcctagt      6660
catgcgctac cgcaacctga tcgagggcga agcatccgcc ggttcctaat gtacggagca      6720
gatgctaggg caaattgccc tagcagggga aaaaggtcga aaaggtctct ttcctgtgga      6780
tagcacgtac attgggaacc caaagccgta cattgggaac cggaacccgt acattgggaa      6840
cccaaagccg tacattggga accggtcaca catgtaagtg actgatataa aagagaaaaa      6900
aggcgatttt tccgcctaaa actctttaaa acttattaaa actcttaaaa cccgcctggc      6960
ctgtgcataa ctgtctggcc agcgcacagc cgaagagctg caaaaagcgc ctacccttcg      7020
gtcgctgcgc tccctacgcc ccgccgcttc gcgtcggcct atcgcggccg ctggccgctc      7080
aaaaatggct ggcctacggc caggcaatct accaggcgc ggacaagccg cgccgtcgcc      7140
actcgaccgc cggcgcccac atcaaggcac cctgcctcgc gcgtttcggt gatgacggtg      7200
aaaacctctg acacatgcag ctcccggaga cggtcacagc ttgtctgtaa gcggatgccg      7260
ggagcagaca agcccgtcag ggcgcgtcag cgggtgttgg cgggtgtcgg ggcgcagcca      7320
tgacccagtc acgtagcgat agcggagtgt atactggctt aactatgcgg catcagagca      7380
gattgtactg agagtgcacc atatgcggtg tgaaataccg cacagatgcg taaggagaaa      7440
ataccgcatc aggcgctctt ccgcttcctc gctcactgac tcgctgcgct cggtcgttcg      7500
gctgcggcga gcggtatcag ctcactcaaa ggcggtaata cggttatcca cagaatcagg      7560
ggataacgca ggaaagaaca tgtgagcaaa aggccagcaa aaggccagga accgtaaaaa      7620
ggccgcgttg ctggcgtttt tccataggct ccgcccccct gacgagcatc acaaaaatcg      7680
acgctcaagt cagaggtggc gaaacccgac aggactataa agataccagg cgtttccccc      7740
tggaagctcc ctcgtgcgct ctcctgttcc gaccctgccg cttaccggat acctgtccgc      7800
```

```
ctttctccct tcgggaagcg tggcgctttc tcatagctca cgctgtaggt atctcagttc   7860
ggtgtaggtc gttcgctcca agctgggctg tgtgcacgaa ccccccgttc agcccgaccg   7920
ctgcgcctta tccggtaact atcgtcttga gtccaacccg gtaagacacg acttatcgcc   7980
actggcagca gccactggta acaggattag cagagcgagg tatgtaggcg gtgctacaga   8040
gttcttgaag tggtggccta actacggcta cactagaagg acagtatttg gtatctgcgc   8100
tctgctgaag ccagttacct tcggaaaaag agttggtagc tcttgatccg gcaaacaaac   8160
caccgctggt agcggtggtt ttttgtttg caagcagcag attacgcgca gaaaaaagg    8220 atctcaagaa gatcctttga tcttttctac ggggtctgac gctcagtgga acgaaaactc   8280
acgttaaggg attttggtca tgcattctag gtactaaaac aattcatcca gtaaatata    8340 atattttatt ttctcccaat caggcttgat ccccagtaag tcaaaaaata gctcgacata   8400
ctgttcttcc ccgatatcct ccctgatcga ccggacgcag aaggcaatgt cataccactt   8460
gtccgccctg ccgcttctcc caagatcaat aaagccactt actttgccat ctttcacaaa   8520
gatgttgctg tctcccaggt cgccgtggga aaagacaagt tcctcttcgg cttttccgt    8580 ctttaaaaaa tcatacagct cgcgcggatc tttaaatgga gtgtcttctt cccagttttc   8640
gcaatccaca tcggccagat cgttattcag taagtaatcc aattcggcta agcggctgtc   8700
taagctattc gtatagggac aatccgatat gtcgatggag tgaaagagcc tgatgcactc   8760
cgcatacagc tcgataatct tttcagggct ttgttcatct tcatactctt ccgagcaaag   8820
gacgccatcg gcctcactca tgagcagatt gctccagcca tcatgccgtt caaagtgcag   8880
gacctttgga acaggcagct ttccttccag ccatagcatc atgtcctttt cccgttccac   8940
atcataggtg gtcccttat accggctgtc cgtcattttt aaatataggt tttcattttc    9000
tcccaccagc ttatatacct tagcaggaga cattccttcc gtatctttta cgcagcggta   9060
tttttcgatc agtttttca attccggtga tattctcatt ttagccattt attatttcct    9120
tcctcttttc tacagtattt aaagataccc caagaagcta attataacaa gacgaactcc   9180
aattcactgt tccttgcatt ctaaaaccttt aaataccaga aaacagcttt ttcaaagttg   9240
ttttcaaagt tggcgtataa catagtatcg acggagccga ttttgaaacc gcggtgatca   9300
caggcagcaa cgctctgtca tcgttacaat caacatgcta ccctccgcga gatcatccgt    9360
gtttcaaacc cggcagctta gttgccgttc ttccgaatag catcggtaac atgagcaaag   9420
tctgccgcct tacaacggct ctcccgctga cgccgtcccg gactgatggg ctgcctgtat   9480
cgagtggtga ttttgtgccg agctgccggt cggggagctg ttggctggct ggtggcagga   9540
tatattgtgg tgtaaacaaa ttgacgctta gacaacttaa taacacattg cggacgtttt    9600
taatgtactg aattaacgcc gaattaattc ggggatctg gattttagta ctggattttg     9660 gtttaggaa ttagaaattt tattgataga agtattttac aaatacaaat acatactaag     9720
ggtttcttat atgctcaaca catgagcgaa accctatagg aacccctaatt cccttatctg    9780 ggaactactc acacattatt atggagaaac tcgagcttgt cgatcgacag atccggtcgg    9840
catctactct atttctttgc cctcggacga gtgctggggc gtcggttccc actatcggcg   9900
agtacttcta cacagccatc ggtccagacg gccgcgcttc tgcgggcgat ttgtgtacgc    9960
ccgacagtcc cggctccgga tcggacgatt gcgtcgcatc gaccctgcgc ccaagctgca   10020
tcatcgaaat tgccgtcaac caagctctga tagagttggt caagaccaat gcggagcata   10080
tacgcccgga gtcgtggcga tcctgcaagc tccggatgcc tccgctcgaa gtagcgcgtc   10140
```

```
tgctgctcca tacaagccaa ccacggcctc cagaagaaga tgttggcgac ctcgtattgg    10200
gaatccccga acatcgcctc gctccagtca atgaccgctg ttatgcggcc attgtccgtc    10260
aggacattgt tggagccgaa atccgcgtgc acgaggtgcc ggacttcggg gcagtcctcg    10320
gcccaaagca tcagctcatc gagagcctgc gcgacgacg cactgacggt gtcgtccatc     10380
acagtttgcc agtgatacac atggggatca gcaatcgcgc atatgaaatc acgccatgta    10440
gtgtattgac cgattccttg cggtccgaat gggccgaacc cgctcgtctg gctaagatcg    10500
gccgcagcga tcgcatccat agcctccgcg accggttgta aacagcggg cagttcggtt      10560 tcaggcaggt cttgcaacgt gacaccctgt gcacggcggg agatgcaata ggtcaggctc    10620
tcgctaaact ccccaatgtc aagcacttcc ggaatcggga gcgcggccga tgcaaagtgc    10680
cgataaacat aacgatcttt gtagaaacca tcggcgcagc tatttacccg caggacatat    10740
ccacgccctc ctacatcgaa gctgaaagca cgagattctt cgccctccga gagctgcatc    10800
aggtcggaga cgctgtcgaa cttttcgatc agaaacttct cgacagacgt cgcggtgagt    10860
tcaggctttt tcatatctca ttgccccccg ggatctgcga aagctcgaga gagatagatt    10920
tgtagagaga gactggtgat ttcagcgtgt cctctccaaa tgaaatgaac ttccttatat    10980
agaggaaggt cttgcgaagg atagtgggat tgtgcgtcat cccttacgtc agtggagata    11040
tcacatcaat ccacttgctt tgaagacgtg gttggaacgt cttctttttc cacgatgctc    11100
ctcgtgggtg ggggtccatc tttgggacca ctgtcggcag aggcatcttg aacgatagcc    11160
tttcctttat cgcaatgatg gcatttgtag gtgccacctt ccttttctac tgtccttttg    11220
atgaagtgac agatagctgg gcaatggaat ccgaggaggt ttcccgatat tacccttgt     11280 tgaaaagtct caatagccct ttggtcttct gagactgtat ctttgatatt cttggagtag    11340
acgagagtgt cgtgctccac catgttatca catcaatcca cttgctttga agacgtggtt    11400
ggaacgtctt cttttccac gatgctcctc gtgggtgggg gtccatcttt gggaccactg      11460
tcggcagagg catcttgaac gatagccttt cctttatcgc aatgatggca tttgtaggtg    11520
ccaccttcct tttctactgt ccttttgatg aagtgacaga tagctgggca atggaatccg    11580
aggaggtttc ccgatattac cctttgttga aaagtctcaa tagcccttg gtcttctgag     11640 actgtatctt tgatattctt ggagtagacg agagtgtcgt gctccaccat gttggcaagc    11700
tgctctagcc aatacgcaaa ccgcctctcc ccgcgcgttg gccgattcat taatgcagct    11760
ggcacgacag gtttcccgac tggaaagcgg gcagtgagcg caacgcaatt aatgtgagtt    11820
agctcactca ttaggcaccc caggctttac actttatgct tccggctcgt atgttgtgtg    11880
gaattgtgag cggataacaa tttcacacag gaaacagcta tgaccatgat tacg          11934
```

<210> SEQ ID NO 2
<211> LENGTH: 696
<212> TYPE: DNA
<213> ORGANISM: Oryza sativa

<400> SEQUENCE: 2

```
gagtatggcc tcatccccgt caccggtctc gcccccctcg gcgccctcca cacagagaaa     60
acgaggctcc tccacagact ccattggcat gtatgcagtt caatgttgtg agtgtcacaa    120
atggcgcaag gttccgacga aggatgaatt tgagacaatt cgtgagaatt tcactgagga    180
gccatggcac tgcagtagaa gacctgactg ctcgtgtgaa gaccctgctg acatcgaata    240
tgatagcagc cgtatatggg tccttgacaa gcctaacata ccaaagcctc cagcaggaac    300
tgagagacta gtgattatga gaggtgattt gtctaaaatg gataccgact atgtcatgcc    360
```

```
aaatgggaag cgtgtaagat gcactgcaga ggtggataag ttccttgagg ccaacccgca    420
gtacaaagat cgcttttcag ttgaaagctt cagctttaca acaccaaaga ttgtcgagga    480
aactgtttct cacaactccg tgtggaagtc tggaaaggct aagaagcagg acaagataaa    540
tgctttgagc aataacaatt aatttctttc aaaagacttt atattatgct taggtgatgc    600
tcatctcagg ttgtggtgct accctcatct actttgtggg ctggtcaaat ctgtttatat    660
ttgcacttag tctgttcggt ctctgtgatc tgtgtg                              696

<210> SEQ ID NO 3
<211> LENGTH: 558
<212> TYPE: DNA
<213> ORGANISM: Oryza sativa

<400> SEQUENCE: 3
atggcctcat ccccgtcacc ggtctcgccc cctcggcgc cctccacaca gagaaaacga     60
ggctcctcca cagactccat tggcatgtat gcagttcaat gttgtgagtg tcacaaatgg    120
cgcaaggttc cgacgaagga tgaatttgag acaattcgtg agaatttcac tgaggagcca    180
tggcactgca gtagaagacc tgactgctcg tgtgaagacc ctgctgacat cgaatatgat    240
agcagccgta tatgggtcct tgacaagcct aacataccaa agcctccagc aggaactgag    300
agactagtga ttatgagagg tgatttgtct aaaatggata cctactatgt catgccaaat    360
gggaagcgtg taagatgcac tgcagaggtg gataagttcc ttgaggccaa cccgcagtac    420
aaagatcgct tttcagttga agcttcagc tttacaacac caaagattgt cgaggaaact    480
gtttctcaca actccgtgtg gaagtctgga aaggctaaga agcaggacaa gataaatgct    540
ttgagcaata acaattaa                                                 558

<210> SEQ ID NO 4
<211> LENGTH: 185
<212> TYPE: PRT
<213> ORGANISM: Oryza sativa

<400> SEQUENCE: 4

Met Ala Ser Ser Pro Ser Pro Val Ser Pro Ser Ala Pro Ser Thr
1               5                   10                  15

Gln Arg Lys Arg Gly Ser Ser Thr Asp Ser Ile Gly Met Tyr Ala Val
            20                  25                  30

Gln Cys Cys Glu Cys His Lys Trp Arg Lys Val Pro Thr Lys Asp Glu
        35                  40                  45

Phe Glu Thr Ile Arg Glu Asn Phe Thr Glu Glu Pro Trp His Cys Ser
    50                  55                  60

Arg Arg Pro Asp Cys Ser Cys Glu Asp Pro Ala Asp Ile Glu Tyr Asp
65                  70                  75                  80

Ser Ser Arg Ile Trp Val Leu Asp Lys Pro Asn Ile Pro Lys Pro Pro
                85                  90                  95

Ala Gly Thr Glu Arg Leu Val Ile Met Arg Gly Asp Leu Ser Lys Met
            100                 105                 110

Asp Thr Tyr Tyr Val Met Pro Asn Gly Lys Arg Val Arg Cys Thr Ala
        115                 120                 125

Glu Val Asp Lys Phe Leu Glu Ala Asn Pro Gln Tyr Lys Asp Arg Phe
    130                 135                 140

Ser Val Glu Ser Phe Ser Phe Thr Thr Pro Lys Ile Val Glu Glu Thr
145                 150                 155                 160
```

```
Val Ser His Asn Ser Val Trp Lys Ser Gly Lys Ala Lys Lys Gln Asp
            165                 170                 175

Lys Ile Asn Ala Leu Ser Asn Asn Asn
            180                 185
```

<210> SEQ ID NO 5
<211> LENGTH: 929
<212> TYPE: DNA
<213> ORGANISM: Oryza sativa

<400> SEQUENCE: 5

```
gcgtgcggaa tctgtagtaa actagtaatc catccccgat cggcggcgat gcagaacccg    60
ccgagccacc ccgttgacct gccgctggcg gcggcgccgc cgccggtgaa ggcgccgacc   120
ccgcgccccc ccacgccggc gtcgctgcag ccggagtccc cggggtgtt cttcacggcc    180
gccgcggcgg ccgccccggt cgggtcctcg caccgccgca tcgccatcgc cgttgacctc   240
tccgacgagt ccgcgtacgc cgtccgctgg gccgtcgcca actacctccg cccccgggac   300
gccgttatac tgctgcacgt ccgccccacc tccgtgctct acggcgccga ctggggctcc   360
gtcgacctct ccctccccgc cgccaaccct aaccctagcg gcgacccgcc gtcggccgag   420
gacgacgctg aggccgcggc ccgcaagatg gaggacgact tcgacgcctt caccgcgtcc   480
aaggccgacg acctggccaa gccgctcaag gacgccggga tcccctacaa gatccacatc   540
gtcaaggatc acgacatgaa ggagaggctc tgcctcgagg tggagaggct tgggctcagc   600
gcggtcatca tggggagcaa gggcttcggc gcctccaggc ggaccagcaa ggggaggctt   660
ggaagcgtca gcgattactg cgtgcaccac tgtgtgtgcc ccgtggtggt ggtgcgtttc   720
cccgacgatg gtgtggcgga gggcggagag gccggtggcg catcggagtt ggcggtgggc   780
gaggaagtgc tgcaccctgt gccagaggag gatgccgagt accatgacgc cactgaagag   840
cacaaggcaa cgtgcgtggt accatcttgt aaataaagga tatgcatggc acatacaagc   900
ctgtatacag ggaacaggtg gcgaatctg                                    929
```

<210> SEQ ID NO 6
<211> LENGTH: 828
<212> TYPE: DNA
<213> ORGANISM: Oryza sativa

<400> SEQUENCE: 6

```
atgcagaacc cgccgagcca ccccgttgac ctgccgctgg cggcggcgcc gccgccggtg    60
aaggcgccga ccccgcgccc ccccacgccg gcgtcgctgc agccggagtc ccggggggtg   120
ttcttcacgg ccgccgcggc ggccgccccg gtcgggtcct cgcaccgccg catcgccatc   180
gccgttgacc tctccgacga gtccgcgtac gccgtccgct gggccgtcgc caactacctc   240
cgcccccggg gacgccgtta tactgctgca cgtccgcccc acctccgtgc tctacggcgcc   300
gactggggct ccgtcgacct ctccctcccc gccgccaacc ctaaccctag cggcgacccg   360
ccgtcggccg aggacgacgc tgaggccgcg gcccgcaaga tggaggacga cttcgacgcc   420
ttcaccgcgt ccaaggccga cgacctggcc aagccgctca aggacgccgg gatcccctac   480
aagatccaca tcgtcaagga tcacgacatg aaggagaggc tctgcctcga ggtggagagg   540
cttgggctca gcgcggtcat catggggagc aagggcttcg gcgcctccag gcggaccagc   600
aaggggaggc ttggaagcgt cagcgattac tgcgtgcacc actgtgtgtg ccccgtggtg   660
gtggtgcgtt tccccgacga tggtgtggcg gagggcggag aggccggtgg cgcatcggag   720
ttggcggtgg gcgaggaagt gctgcaccct gtgccagagg aggatgccga gtaccatgac   780
```
gccactgaag agcacaaggc aacgtgcgtg gtaccatctt gtaaataa          828

<210> SEQ ID NO 7
<211> LENGTH: 275
<212> TYPE: PRT
<213> ORGANISM: Oryza sativa

<400> SEQUENCE: 7

```
Met Gln Asn Pro Pro Ser His Pro Val Asp Leu Pro Leu Ala Ala Ala
1               5                   10                  15

Pro Pro Val Lys Ala Pro Thr Pro Arg Pro Pro Thr Pro Ala Ser
            20                  25                  30

Leu Gln Pro Glu Ser Pro Gly Val Phe Phe Thr Ala Ala Ala Ala
            35                  40                  45

Ala Pro Val Gly Ser Ser His Arg Arg Ile Ala Ile Ala Val Asp Leu
    50                  55                  60

Ser Asp Glu Ser Ala Tyr Ala Val Arg Trp Ala Val Ala Asn Tyr Leu
65                  70                  75                  80

Arg Pro Gly Asp Ala Val Ile Leu Leu His Val Arg Pro Thr Ser Val
                85                  90                  95

Leu Tyr Gly Ala Asp Trp Gly Ser Val Asp Leu Ser Leu Pro Ala Ala
            100                 105                 110

Asn Pro Asn Pro Ser Gly Asp Pro Ser Ala Glu Asp Ala Glu
            115                 120                 125

Ala Ala Ala Arg Lys Met Glu Asp Asp Phe Asp Ala Phe Thr Ala Ser
    130                 135                 140

Lys Ala Asp Asp Leu Ala Lys Pro Leu Lys Asp Ala Gly Ile Pro Tyr
145                 150                 155                 160

Lys Ile His Ile Val Lys Asp His Asp Met Lys Glu Arg Leu Cys Leu
                165                 170                 175

Glu Val Glu Arg Leu Gly Leu Ser Ala Val Ile Met Gly Ser Lys Gly
            180                 185                 190

Phe Gly Ala Ser Arg Arg Thr Ser Lys Gly Arg Leu Gly Ser Val Ser
        195                 200                 205

Asp Tyr Cys Val His His Cys Val Cys Pro Val Val Val Arg Phe
    210                 215                 220

Pro Asp Asp Gly Val Ala Glu Gly Gly Glu Ala Gly Gly Ala Ser Glu
225                 230                 235                 240

Leu Ala Val Gly Glu Glu Val Leu His Pro Val Pro Glu Glu Asp Ala
                245                 250                 255

Glu Tyr His Asp Ala Thr Glu Glu His Lys Ala Thr Cys Val Val Pro
            260                 265                 270

Ser Cys Lys
        275
```

<210> SEQ ID NO 8
<211> LENGTH: 24
<212> TYPE: DNA
<213> ORGANISM: Artificial Sequence
<220> FEATURE:
<223> OTHER INFORMATION: Forward primer for cloning cDNA of OsMBD1 gene

<400> SEQUENCE: 8
gagtatggcc tcatccccgt cacc          24

<210> SEQ ID NO 9

```
<211> LENGTH: 27
<212> TYPE: DNA
<213> ORGANISM: Artificial Sequence
<220> FEATURE:
<223> OTHER INFORMATION: Reverse primer for cloning cDNA of OsMBD1 gene

<400> SEQUENCE: 9
cacacagatc acagagaccg aacagac                                              27

<210> SEQ ID NO 10
<211> LENGTH: 30
<212> TYPE: DNA
<213> ORGANISM: Artificial Sequence
<220> FEATURE:
<223> OTHER INFORMATION: Forward primer for cloning cDNA of OsUSP1 gene

<400> SEQUENCE: 10
gcgtgcggaa tctgtagtaa actagtaatc                                           30

<210> SEQ ID NO 11
<211> LENGTH: 27
<212> TYPE: DNA
<213> ORGANISM: Artificial Sequence
<220> FEATURE:
<223> OTHER INFORMATION: Reverse primer for cloning cDNA of OsUSP1 gene

<400> SEQUENCE: 11
cagattcgcc acctgttccc tgtatac                                              27

<210> SEQ ID NO 12
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsMBD1 gene

<400> SEQUENCE: 12
ctgactgctc gtgtgaagac                                                      20

<210> SEQ ID NO 13
<211> LENGTH: 21
<212> TYPE: DNA
<213> ORGANISM: Artificial Sequence
<220> FEATURE:
<223> OTHER INFORMATION: Reverse primer for real-time RT-PCR analysis of
      OsMBD1 gene

<400> SEQUENCE: 13
tggaggcttt ggtatgttag g                                                    21

<210> SEQ ID NO 14
<211> LENGTH: 21
<212> TYPE: DNA
<213> ORGANISM: Artificial Sequence
<220> FEATURE:
<223> OTHER INFORMATION: Forward primer for real-time RT-PCR analysis of
      OsUSP1 gene

<400> SEQUENCE: 14
ccctacaaga tccacatcgt c                                                    21

<210> SEQ ID NO 15
<211> LENGTH: 18
<212> TYPE: DNA
<213> ORGANISM: Artificial Sequence
<220> FEATURE:
```

-continued

```
<223> OTHER INFORMATION: Reverse primer for real-time RT-PCR analysis of
      OsUSP1 gene

<400> SEQUENCE: 15
cttccaagcc tccccttg                                                    18
```